(12) United States Patent
Garcia et al.

(10) Patent No.: US 9,381,217 B2
(45) Date of Patent: Jul. 5, 2016

(54) MICROGELS FOR ENCAPSULATION OF CELLS AND OTHER BIOLOGIC AGENTS

(71) Applicant: Georgia Tech Research Corporation, Atlanta, GA (US)

(72) Inventors: Andres Garcia, Atlanta, GA (US); Devon Headen, Atlanta, GA (US); Edward A. Phelps, Atlanta, GA (US); Guillaume A. Aubry, Atlanta, GA (US); Hang Lu, Atlanta, GA (US); Cristina Gonzalez Garcia, Valencia (ES)

(73) Assignee: Georgia Tech Research Corporation, Atlanta, GA (US)

( * ) Notice: Subject to any disclaimer, the term of this patent is extended or adjusted under 35 U.S.C. 154(b) by 23 days.

(21) Appl. No.: 14/481,407

(22) Filed: Sep. 9, 2014

(65) Prior Publication Data
US 2015/0071997 A1    Mar. 12, 2015

Related U.S. Application Data

(60) Provisional application No. 61/875,287, filed on Sep. 9, 2013.

(51) Int. Cl.
| | |
|---|---|
| *A61K 9/50* | (2006.01) |
| *A61K 38/38* | (2006.01) |
| *A61K 35/28* | (2015.01) |
| *A61K 38/28* | (2006.01) |
| *A61K 35/39* | (2015.01) |
| *A61K 39/44* | (2006.01) |
| *A61K 31/7004* | (2006.01) |
| *A61K 9/00* | (2006.01) |
| *A61K 38/00* | (2006.01) |

(52) U.S. Cl.
CPC ............ *A61K 35/28* (2013.01); *A61K 9/0024* (2013.01); *A61K 9/5031* (2013.01); *A61K 31/7004* (2013.01); *A61K 35/39* (2013.01); *A61K 39/44* (2013.01); *A61K 38/00* (2013.01)

(58) Field of Classification Search
CPC ... A61K 35/28; A61K 39/44; A61K 31/7004; A61K 35/39; A61K 9/0024; A61K 9/5031; A61K 38/00
See application file for complete search history.

(56) References Cited

PUBLICATIONS

Allazetta, et al., "Microfluidic synthesis of cell-type-specific artificial extracellular matrix hydrogels", Biomacromolecules, 14(4):1122-31 (2013).
Blasi, et al., "Conformal polymer coatings for pancreatic islets transplantation", Int J Pharm, 440(2):141-7 (2013).
Choi, et al., "Generation of monodisperse alginate microbeads and in situ encapsulation of cell in microfluidic device", Biomed Microdevices, 9(6):855-62 (2007).
Chung, et al., "Optofluidic maskless lithography system for real-time synthesisof photopolymerized microstructures in microfluidic channels", Applied Physics Letters, 91:041106 (2007).
Jun, et al., "Microfluidics-generated pancreatic islet microfibers for enhanced immunoprotection", Biomaterials, 34(33):8122-30 (2013).
Kesselman, et al., "Synthesis of monodisperse, covalently cross-linked, degradable "smart" microgels using microfluidics", Small, 8(7):1092-8 (2012).
Koster, et al., "Drop-based microfluidic devices for encapsulation of single cells", Lab Chip, 8(7):1110-5 (2008).
Langer, et al., "Designing materials for biology and medicine", Nature, 428 (6982):487-92 (2004), abstract only.
Lienemann, et al., "A versatile approach to engineering biomolecule-presenting cellular microenvironments.", Advanced Healthcare Materials, 2(2):292-6 (2013).
Lutolf, et al, "Synthetic biomaterials as instructive extracellular microenvironments for morphogenesis in tissue engineering", Nat Biotechnol, 23 (1):47-55 (2005).
Lutolf, et al., "Designing materials to direct stem-cell fate", Nature, 462 (7272):433-41 (2009).
Okhamafe, et al., "Modulation of protein release from chitosan-alginate microcapsules using the pH-sensitive polymer hydroxypropyl methylcellulose acetate succinate", J. Microencapsul., 13(5):497-508 (1997).
Onoe, et al., "Metre-long cell-laden microfibres exhibit tissue morphologies and functions", Nature Materials, 12(6):584-90 (2013).
Panda, et al., "Stop-flow lithography to generate cell-laden microgel particles", Lab Chip, 8(7):1056-61 (2008).
Peppas, et al., "New challenges in biomaterials", Science, 263(5154):1715-20 (1994).
Phelps, et al., "Vasculogenic bio-synthetic hydrogel for enhancement of pancreatic islet engraftment and function in type 1 diabetes", Biomaterials, 34 (19):4602-11 (2013).
Ranganath, et al., "Harnessing the mesenchymal stem cell secretome for the treatment of cardiovascular disease", Cell Stem Cell, 10(3):244-58 (2012).
Rossow, et al., "Controlled synthesis of cell-laden microgels by radical-free gelation in droplet microfluidics", J Am Chem Soc., 134(10):4983-9 (2012).

(Continued)

*Primary Examiner* — Ali Soroush
*Assistant Examiner* — Genevieve S Alley
(74) *Attorney, Agent, or Firm* — Pabst Patent Group LLP

(57) ABSTRACT

Methods of encapsulating cargo in a microgel droplet, microgel droplets prepared according the provided methods, and methods of use thereof are disclosed. The methods of preparing cargo-encapsulated microgels generally include flowing through a flow-focusing nozzle of a microfluidic device a macromer phase, an oil phase, and a crosslinker phase to form microgel droplets by oil-water emulsion. The phases are pumped, injected, or flowed through the microfluidic device such that as the macromer phase approaches the flow focusing nozzle, the co-flowing oil phase shields the macromer from contact with the crosslinker phase until flow instability occurs and macromer phase droplets form. After flow instability occurs, the crosslinker diffuses from the crosslinker phase into the droplets in an effective amount to covalently crosslink the macromer into a microgel network encapsulating the cargo in the crosslinked macromer. Microgels prepared according to the disclosed methods and methods of use thereof are also provided.

18 Claims, 7 Drawing Sheets

(56) References Cited

PUBLICATIONS

Santos, et al., "Therapeutic cell encapsulation: ten steps towards clinical translation", J. Control, 170:1-14 (2013).

Teramura, et al. "Microencapsulation of cells, including islets, within stable ultra-thin membranes of maleimide-conjugated PEG-lipid with multifunctional crosslinkers", Biomaterials, 34(11):2683-93 (2013) (Abstract Only).

Tumarkin, et al., "Microfluidic generation of microgels from synthetic and natural polymers", Chem Soc Rev., 38(8):2161-8 (2009).

Um, et al., "Continuous generation of hydrogel beads and encapsulation of biological materials using a microfluidic droplet-merging channel", Microfluid Nanofluid, 5:541-9 (2008).

Velasco, et al., "Microfluidic encapsulation of cells in polymer microgels", Small, 8(11):1633-42 (2012).

Wang, et al., "An encapsulation system for the immunoisolation of pancreatic islets", Nature Biotechnology, 15:358 (1997).

MICROGELS FOR ENCAPSULATION OF CELLS AND OTHER BIOLOGIC AGENTS

CROSS-REFERENCE TO RELATED APPLICATIONS

This application claims priority to and benefit of U.S. Provisional Patent Application No. 61/875,287 filed on Sep. 9, 2013, and where permissible is incorporated by reference in its entirety.

REFERENCE TO SEQUENCE LISTING

The Sequence Listing submitted Sep. 9, 2014 as a text file named "GTRC_6467_ST25.txt," created on Sep. 9, 2014, and having a size of 1,723 bytes is hereby incorporated by reference pursuant to 37 C.F.R. §1.52(e)(5).

FIELD OF THE INVENTION

The invention is generally directed to methods of encapsulating cells and other bioactive agents in microgel droplets, microgel droplet therefrom, and methods of use thereof.

BACKGROUND OF THE INVENTION

Hydrogel microencapsulation of cells is a promising strategy for immunoprotection after transplantation. Since the development of alginate-poly-L-lysine encapsulation by Lim and Sun in 1980 (Lim, et al., *Science* 210(4472):908-10 (1980)), their approach has remained the standard for cell encapsulation, although major efforts have led to improvements (T. Wang, et al., *Nature Biotechnology*, 15:358 (1997)). The ease of alginate microencapsulation, along with alginate's inherent biotolerance in vivo, has led to its prevalence (E. Santos, et al., *J. Control*, 170:1 (2013)), even though the ability to control local cellular environment via incorporation of bioactive molecules (e.g., adhesive peptides) is limited. Highly tunable, synthetic hydrogel encapsulation is attractive for various regenerative medicine applications (Lutolf, et al, *Nat Biotechnol*, 23(1):47-55 (2005), Peppas, et al., *Science*, 263(5154):1715-20 (1994); Langer, et al., *Nature*, 428(6982):487-92 (2004)), not only for immunoisolation, but also for directing cell behavior and fate (Lutolf, et al, *Nat Biotechnol*, 23(1):47-55 (2005)). Several groups have developed more complex encapsulation configurations, such as cell encapsulation in natural hydrogel fibers (Onoe, et al., *Nature Materials*, 12(6):584-90 (2013); Jun, et al., *Biomaterials*, 34(33):8122-30 (2013)), but the benefits of added geometric complexity remain to be established.

Minimization of encapsulation volume is also important in many regenerative medicine scenarios, including pancreatic islet transplantation. In an effort to reduce the high polydispersity present in electrostatically generated alginate droplets with diameters <200 μm (Goosen, et al., *J. Microencapsul.*, 13(5):497-508 (1997)), microfluidic droplet generation has been explored (Choi, et al., *Biomed Microdevices*, 9(6):855-62 (2007); Tan, et al., *Advanced Materials*, 19:2696 (2007); Um, et al., *Microfluid Nanofluid*, 5:541 (2008)). Microfluidic devices have also been used to generate synthetic hydrogel particles (Rossow, et al., *Journal of the American Chemical Society*, 134(10):4983-9 (2012), Velasco, et al., *Small*, 8(11):1633-42 (2012), Allazetta, et al., *Biomacromolecules*, 14(4):1122-31 (2013), Panda, et al., *Lab Chip*, 8(7):1056-61 (2008), Chung, et al., *Applied Physics Letters*, 91:041106 (2007)). Weitz established encapsulation of cells inside emulsions for high throughput cell-based assays Koster, et al., *Lab Chip*, 8(7):1110-5 (2008). However, translating this work into covalently crosslinking of microgels within microfluidic devices adds significant complexity because polymer precursors must be liquid while flowing through the focusing nozzle, but droplets must crosslink rapidly after being generated to prevent them from merging.

Synthetic polymer microgels have been generated, including cell-laden microgels (Rossow, et al., *Journal of the American Chemical Society*, 134(10):4983-9 (2012), Velasco, et al., *Small*, 8(11):1633-42 (2012), Allazetta, et al., *Biomacromolecules*, 14(4):1122-31 (2013), Panda, et al., *Lab Chip*, 8(7):1056-61 (2008), Chung, et al., *Applied Physics Letters*, 91:041106 (2007) Kesselman, et al., *Small*, 8(7):1092-8 (2012), Tumarkin, et al., *Chemical Society Reviews*, 38(8):2161-8 (2009)). However, even for synthetic polymer encapsulation, control of cellular microenvironment by functionalization of polymers with bioactive molecules remains a significant challenge. Most of these schemes require crosslinking using UV-based free radical polymerization, resulting in potentially cytotoxic effects on encapsulated cells. Although cell encapsulation in synthetic microgels crosslinked without free radicals has been reported, the polymer cannot easily be functionalized with bioactive molecules (Rossow, et al., *Journal of the American Chemical Society*, 134(10):4983-9 (2012), Kesselman, et al., *Small*, 8(7):1092-8 (2012)). This major limitation makes the maintenance of cells requiring adhesive ligands for viability and function difficult. Lutolf devised a microfluidic scheme to generate surface-modifiable synthetic microgels that does not utilize free radical polymerization, but neither bulk modification with bioactive molecules nor cell encapsulation was shown (Allazetta, et al., *Biomacromolecules*, 14(4):1122-31 (2013), Panda, et al., *Lab Chip*, 8(7):1056-61 (2008), Chung, et al., *Applied Physics Letters*, 91:041106 (2007)).

Microfluidic encapsulation of large clusters of cells, such as human islets, is more challenging than single cell encapsulation, because the larger particles tend to clog microfluidic channels. To minimize encapsulation volume while avoiding microfluidics altogether, investigators have explored conformal coating of islets (Blasi, et al., *International Journal of Pharmaceutics*, 440(2):141-7 (2013), Teramura, et al., *Biomaterials*, 34(11):2683-93 (2013)). Whereas conformal coating minimizes transplant volume, the immunoisolation potential of such thin polymer membranes remains unknown.

Thus there remains a need for improved, biocompatible methods of encapsulating cells and other biological agents in microgels.

It is therefore an object of the invention to provide a tunable, biocompatible platform for packaging cells and/or other biological agents, including, but not limited to, peptides, proteins, nucleic acids, and other biomolecules, into microgels.

It is a further object of the invention to provide a tunable, biocompatible platform for packaging multiple cells, for example cell clusters or islets, into a single microgel droplet.

It is another object of the invention to provide compositions including microgel encapsulated cells and other biological agents.

It is another object of the invention to provide methods of using microgel encapsulated cells and both biological agents.

SUMMARY OF THE INVENTION

Methods of encapsulating cargo in a microgel droplet, microgel droplets prepared according to the provided methods, and methods of using the microgels are disclosed. The methods of preparing cargo-encapsulated microgels generally include flowing a macromer phase, an oil phase, and a crosslinker phase through a flow focusing nozzle of a microfluidic device to form microgel droplets by oil-water emulsion. The macromer phase typically includes a macromer and a cargo in aqueous buffer; the oil phase typically includes an oil and a surfactant; and the crosslinker phase includes an oil, a surfactant, and a crosslinking agent. The phases are pumped, injected, or passaged through the microfluidic device such that as the macromer phase approaches the flow focusing nozzle, the co-flowing oil phase shields the macromer from contact with the crosslinker phase until flow instability occurs and macromer phase droplets form. After flow instability occurs, the crosslinker diffuses from the crosslinker phase into the droplets in an effective amount to covalently crosslink the macromer into a microgel network encapsulating the cargo in the crosslinked macromer.

The method can be fine-tuned to control the size and permeability of the microgel droplet. For example, the nozzle size and flow rates can be selected to produce droplets of a size between about 10 μm and 1,000 μm, inclusive. In a particular embodiment, the macromer is a four arm maleimide-linked polyethylene glycol (PEG-4MAL). A preferred crosslinker includes a thiol that can be covalent crosslinked to the maleimide by a Michael-type additional reaction, for example, dithiothreitol (DTT), or a biodegradable peptide crosslinker. In some embodiments, the peptide includes a cleavage site for one or more proteases or other enzymes. In this way, release of the cargo from the microgel can be controlled by contacting the microgels with the protease or enzyme. The contacting with the protease or enzyme can occur in vivo. In some embodiments, the protease or enzyme is upregulated in a disease or disorder state, or in diseased or dysfunctional tissue such that cargo is released from the microgel when the disease or disorder is active and/or when the microgel comes in close proximity of the diseased or dysfunctional tissue. Exemplary peptide crosslinkers include, but are not limited to, peptides including the amino acids of SEQ ID NOS:4, 5, or 6, or a variant thereof with at least 70%, 80%, 85%, 90%, 95%, or more sequence identity to SEQ ID NO:4, 5, or 6, and which preferably includes two cysteines, and can be cleaved by one or more proteases.

The permeability can be adjusted by, for example, altering the size of the macromer and type of crosslinker used. The Examples below illustrate that a microgel network formed of 10 kDa PEG-4MAL is generally impermeable to macromolecules such as IgG, while a network formed of a 20 kDa PEG-4MAL is somewhat more permeable to IgG. The permeability of the microgel can be adjusted based on the application. For example, the permeability of the microgel can be selected based on a desired release rate of a bioactive agent encapsulated therein. In other embodiments, the permeability is selected to prevent antibodies and immune cell from reaching encapsulated cells, while nutrients, signaling molecules, and waste can be transported across the microgel capsule.

The methods can be used to encapsulate a single cell, clusters of cells including islets, and other bioactive agents including, but not limited to, proteins, peptides, amino acids, nucleic acids, carbohydrates, lipids, small molecules, or combinations thereof. The method is particularly well suited for preparing viable, microencapsulated monodispersed multicell islets. The methods are also particular useful for drug delivery, particularly of macromolecular drugs such as peptide and protein based therapeutic agents.

In some embodiments, the macromer is functionalized prior to crosslinking. In a particularly preferred embodiment, this is accomplished by reacting a bioactive active agent with a thiol group (e.g., a protein or peptide with cysteine) with a maleimide on the macromere prior to crosslinking. In some examples, the functionalize moiety is a peptide including an RGD ligand for integrins to enhance cell adhesion and survival. In some embodiments, the bioactive agent is a therapeutic drug which can be released from the microgel by a protease or other enzymes in vivo.

Microgel droplets prepared according to the disclosed methods can be used for myriad of therapeutic applications by administering an effective amount of the microgels to a subject in need thereof. For example, in a particular embodiment, the microgels encapsulate insulin secreting pancreatic beta cell islets which can be transplanted into a subject to treat diabetes. In another embodiment, the microgel serves as a drug delivery vehicle or drug deport and can be used to administer a subject an effective amount of a bioactive agent to treat a disease or disorder such as cancer or an infection.

DETAILED DESCRIPTION OF THE INVENTION

I. Definitions

Figures 1A, 1B:
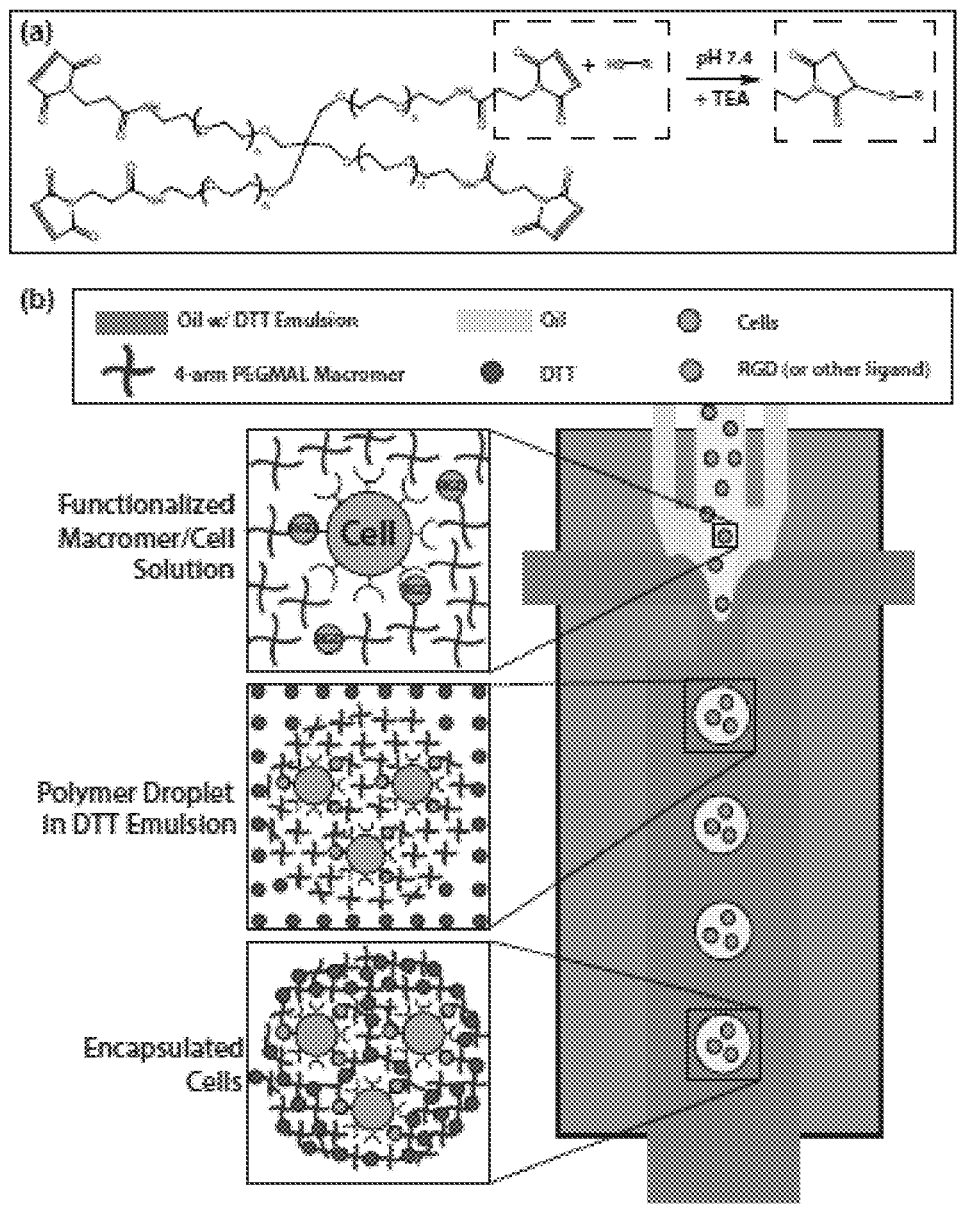
FIG. 1A is reaction diagram showing the structure of a PEG-4MAL macromer including a 4-arm branched PEG backbone modified with a maleimide group terminating each arm. At physiological pH, free thiol-containing molecules undergo a Michael-type addition reaction with maleimides, forming a covalent bond to macromer. This reaction is facilitated by nucleophilic buffers such as triethanolamine (TEA), and can be used to either functionalize the macromer or crosslink macromer into a hydrogel network.
FIG. 1B is a schematic of a microfluidic device with flow focusing geometry utilized to produce microgels according to the disclosed methods. A co-flowing oil phase shields an aqueous macromer solution, containing cells and/or other bioactive agents such a proteins, from the crosslinker-containing oil phase as the macromer solution approaches the flow focusing nozzle. After droplet formation, the crosslinker (e.g., DTT) emulsion rapidly crosslinks macromere solution into cell- or protein-laden microgels.
Figure 2A:
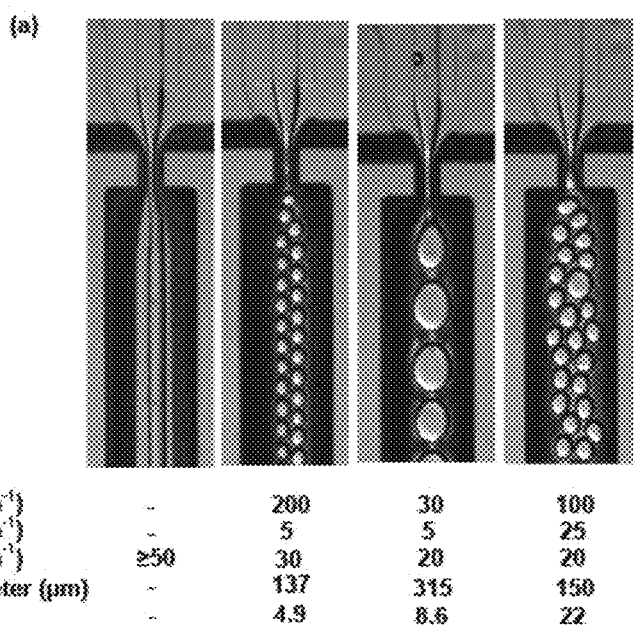
FIG. 2A is a series of representative images and quantification of microgel diameters for corresponding varied flow rates.
Figures 2B, 2C, 2D, 2E:
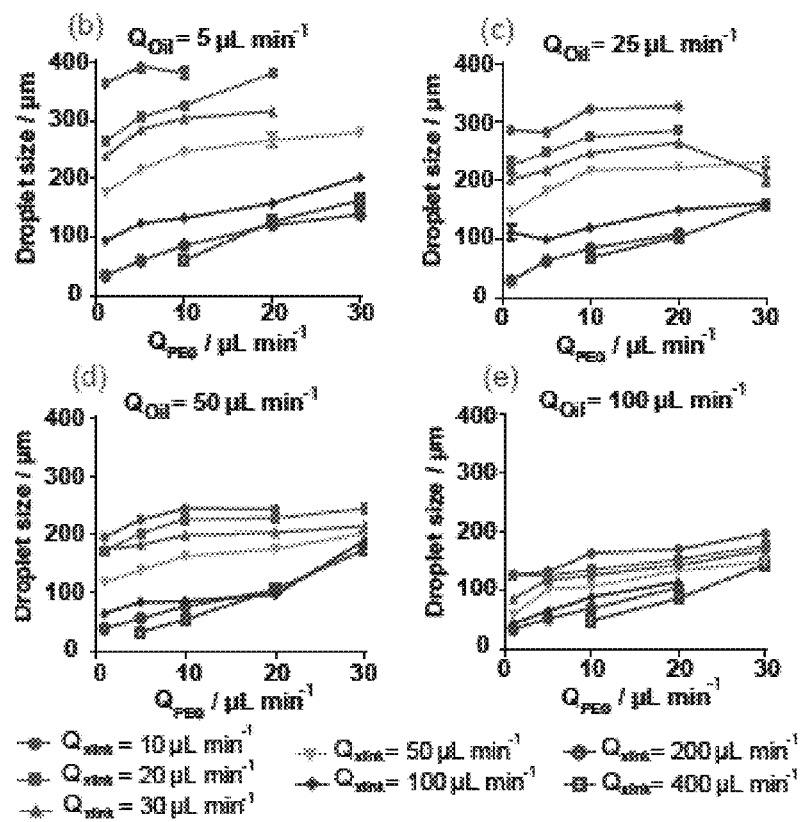
FIGS. 2B-2E are line graphs showing the droplet size (μm) as a function of various macromer phase flow rates (1, 5, 10, 20, 30 $Q_{PEG}$/μmin$^{-1}$) and crosslinker phase flow rates (10, 20, 30, 50, 100, 200, 400 $Q_{xlink}$/μmin$^{-1}$) for oil phase flow rates ($Q_{Oil}$) of 5 μmin$^{-1}$ (2B), 25 μmin$^{-1}$ (2C), 50 μmin$^{-1}$ (2D), 100 μmin$^{-1}$ (2E). Mean and standard error were plotted as calculated from a minimum of 30 measurements for each condition.

As used herein, "polymer" refers to a molecule consisting of a number of repeating units.

As used herein, "repeat unit" refers to the fundamental recurring unit of a polymer.

As used herein, "monomer" refers to the smaller molecule(s) that are used to prepare a polymer. It may or may not be equivalent to the repeat unit.

As used herein, "macromer" and "macromonomer" refers to any polymer or oligomer that has a functional group that can take part in further polymerization.

As used herein, "microgel" refers to a gel formed from a network of microscopic filaments of polymer or macromer.

As used herein, "subject or patient" refers to a mammal, primate and preferably a human.

As used herein, "implant", refers widely to any type of implanted or implantable foreign object or material. Implants also include objects or materials that are nearly identical to non-foreign objects or materials. The implant according to the invention is not limited to any particular shape. The final shape of the implant in the body is decided by the skilled man from the purpose of the treatment.

As used herein, the term "carrier" or "excipient" refers to an organic or inorganic ingredient, natural or synthetic inactive ingredient in a formulation, with which one or more active ingredients are combined.

As used herein, the term "pharmaceutically acceptable" means a non-toxic material that does not interfere with the effectiveness of the biological activity of the active ingredients.

As used herein, the terms "effective amount" or "therapeutically effective amount" means a dosage sufficient to alleviate one or more symptoms of a disorder, disease, or condition being treated, or to otherwise provide a desired pharmacologic and/or physiologic effect. The precise dosage will vary according to a variety of factors such as subject-dependent variables (e.g., age, immune system health, etc.), the disease or disorder being treated, as well as the route of administration and the pharmacokinetics of the agent being administered.

As used herein, the term "prevention" or "preventing" means to administer a composition to a subject or a system at risk for or having a predisposition for one or more symptom caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

II. Platform for Encapsulation of Cells and Other Biological Agents

A modular, two-phase (oil-water) microfluidics-based platform for the generation of hydrogel microsphere (microgel) droplets of controlled size and permeability using is provided. Microgel droplets encapsulating cells and/or other biological agents, such as peptides, proteins, nucleic acids, etc., prepared according to the disclosed platform, and methods of use thereof are also provided.

The platform typically includes a microfluidic device with a flow focusing nozzle and three independent flows: (1) a polymer or macromer phase including a polymer and a cargo, typically cells and/or one or more other bioactive agents, typically in aqueous, physiological buffer; (2) an oil phase containing a surfactant; and (3) a crosslinker phase containing oil and surfactant with an emulsion of crosslinker solution. As used herein "polymer" and "macromer" are used interchangeable to refer to the subunits that are crosslinked to form the microgel. Therefore, the "polymer phase" can be a "macromer phase" and vice versa depending on the subunit that is selected. However, it will be appreciated that the polymer or macromer used in the polymer/macromer phase is capable of being crosslinked or further polymerized by a crosslinker in the crosslinker phase to form a microgel droplet.

A. Methods of Making Microgels

The three phases are flowed or pumped into a microfluidic device with flow focusing geometry. In a particular embodiment, the microfluidic device is a polydimethylsiloxane (PDMS) microchip (Fujii, et al., *Microelectronic Engineering*, 61-62:907-914 (2002)). The three fluid phases can be flowed or pump through the microfluidic device using any suitable means. In preferred embodiments the phases are delivered by pumps, for example syringe pumps. Exemplary microfluidic devices are schematized in FIGS. 1B and 5A.

As the macromer phase approaches the flow-focusing nozzle, a co-flowing continuous phase of oil shields the macromer from contact with the crosslinker phase until flow instability occurs. The crosslinker then rapidly diffuses into droplets, covalently crosslinking the macromer into a microgel network encapsulating the cells or other bioactive agent in the crosslinked polymer. Because crosslinker cannot reach the macromer before flow instability occurs, monodisperse, spherical microgel droplets can be formed in this manner.

Outlet channel length can be used to control the residence time of the generated droplets inside the device. For example, increasing the length of the channel increases the residence time of the generated droplets inside the device. The molar ratio of the macromer:crosslinker and pH of the fluids can be modulated to control the kinetics of the gelation after contact of both phases in the microfluidic device. The length of the channel in combination with the kinetics of gelation can be fine-tuned to ensure microgel formation before the macromer droplets leave the device. The macromer and crosslinker, which are discussed in more detail below, are used in concentrations and ratios that are effective for form microgels.

The platform is used to prepare microgel encapsulated cargo. In the most preferred embodiment, the cargo is cells and/or one or more other bioactive agents. Therefore, oil, surfactant, macromer and crosslinker are typically used in concentrations that are biocompatible with the cells or bioactive agents they are being used to encapsulate. For example, preferably the oil, surfactant, macromer and/or crosslinker does not substantially damage or kill the cells, or substantially reduce, inhibit, or inactive the bioactive agent. Preferably at least 20%, 30%, 40%, 50%, 60%, 70%, 80%, 85%, 90%, 95%, 99%, or more than 99% of the loaded cells remain viable following encapsulation. Preferably at least 20%, 30%, 40%, 50%, 60%, 70%, 80%, 85%, 90%, 95%, 99%, or more than 99% of the loaded bioactive agent remains active or functional following encapsulation.

As discussed herein microgel droplets prepared according the disclosed methods can be polydispersed or monodispersed. Dispersity, as used herein refers to a measure of the heterogeneity of sizes of microgels in a mixture (e.g., a composition including at least two microgel droplets). Therefore, monodispersed compositions are typically composed of microgels that are predominately essentially the same size, while polydispersed compositions are typically composed of microgels of different sizes. In some embodiments, the method can be used to prepare a population of microgels that is at least 50%, 60%, 70%, 75%, 80%, 85%, 90%, 95%, 99%, or more essentially the same size. Therefore, compositions having microgels, wherein at least 50%, 60%, 70%, 75%, 80%, 85%, 90%, 95%, 99% or more of the microgels are at least 50%, 60%, 70%, 75%, 80%, 85%, 90%, 95%, 99%, or more essentially the same size are also provided. Microgels can be considered to be essentially the same size when they are between about 50% and about 150%, or between about 60% and about 140%, or between about 30% and about 130%, or between about 20% and about 120%, or between about 10% and about 110%, or between about 95% and about 105% of the size of a reference microgel or desired microgel size. Preferred sizes depend on the intended use and are discussed in more detail below.

B. Methods of Tuning Microgel Parameters

As illustrated in the Examples below, certain parameters of the microfluidic-based methods of making microgels disclosed herein can be varied to fine tune the permeability and size of the resulting microgels.

1. Permeability

A tunable hydrogel network with selective permeability to biomolecules is can be important for cell microencapsulation, particularly when the microgels are used for encapsulating cells. For example, in transplantation applications, antibodies and immune cells (relatively large objects) should be prevented from reaching encapsulated cells, while nutrients, signaling molecules, and waste (relatively small molecules) should be easily transported across the microgel capsule. Modulating permeably can also be used to control the release kinetics of an encapsulated bioactive agent in drug delivery applications.

For example, analysis of release kinetics detailed in the Examples below show that microgels composed of a 20 kDa macromer PEG-4MAL polymer release nearly 100% of the smaller molecules glucose and insulin. Alternatively, for larger proteins BSA and IgG, the release did not reach 50% of the incorporated amount because these larger molecules remain trapped within the tight network structure of the PEG hydrogel.

The Examples also illustrate that a tighter network mesh of the microgels based on 10 kDa marcomer slowed the release of encapsulated IgG compared to microgels made with 20 kDa macromer. It is believed that not only macromer size, but also other parameters of the composition and method of making the microgel, including, but limited to, the polymer weight % and crosslinking density, can be systematically varied alone or in any combination, to obtain and fine tune desired release kinetics. These parameters can be modulated by varying compositions, such as the macromer and crosslinker as described in more detail below. These release kinetics can be tested using known methods, for example, the protein encapsulation and release assays described in the Examples below.

2. Size

Tunable control of particle size and monodispersity are important for many applications of microgels, and the disclosed microfluidic platform affords this control over a wide range of particle sizes. Typical microencapsulation techniques (e.g. droplet generators using parallel air flow or electrostatic charge) are hindered by the inability to produce capsules small enough for adequate nutrient diffusion to encapsulated cells, because large void spaces within capsules hinder diffusion. An advantageous aspect of the microfluidic technology disclosed herein is the capacity for tailoring of capsule size to cell type. A wide range of cell or particle sizes are able to be encapsulated, from, for example, 300 μm islet cell clusters to 10 μm single cells and smaller, with minimal void space. This results in more advantageous nutrient and therapeutic agent diffusion than similar technologies.

Additionally, the use of synthetic polymers can provide a greater ability to tailor the local environment towards the specific needs of the application. An advantage of this system over alternative methods utilizing synthetic polymers is the maintenance of high islet viability and function. Many alternative synthetic encapsulation schemes utilize or result in components toxic to islets, which consequently limits the success of these techniques.

At least two different parameters, of the disclosed platform, flow rate and channel/nozzle size, can be varied alone, or combination to modulate the microgel size and dispersity.

The Examples below illustrate that using a fixed nozzle size of 300 μm nozzle, microgels with a wide range of sizes, ranging from 20 to 400 μm, could be produced on the same device by varying modulating the macromer phase flow rate between 0 μl/min and 30 μl/min; the oil phase between 5 μl/min and 100 μl/min; and the crosslinker phase between 10 μl/min and 400 μl/min. Although several flow regimes produced microgels with undesirable polydisperse distributions (coefficient of variation, CV>10%), flow rate combinations were identified that produced a range of microgel sizes from 135-325 μm with monodisperse populations (CV<5%) (see FIG. 2A-2E).

Therefore, the flow rates of one or more of the phases can be adjusted to fine tune the size of the microgels that are produced. For example, the flow rate of each of the macromere phase, the oil phase, and crosslinker phase in a microfluidic device is generally "X" nl/min, wherein "X" is an integer between about 100 and about 1,000,000, preferably between about 1,000 and about 500,000, more preferably between about 1,000 and 50,000, inclusive. The flow rate of each of the macromere phase, the oil phase, and crosslinker phase in a microfluidic device can also be "X" μl/min, wherein "X" is an integer between about 1 and about 1,000, preferably between about 1 and about 500, more preferably between about 1 and 50, inclusive. The flow rates can also be adjusted as needed to accommodate the selected nozzle size.

Although a device with fixed geometry is capable of producing a wide range of particle sizes, in preferred embodiments, the nozzle size is selected based on the desired size of the droplets. In preferred embodiments, droplets are generated with diameters that are between about 50% and about 100%, inclusive of the nozzle width to obtain a monodisperse population. For example, a 300 μm nozzle was very effective for producing monodisperse populations in the range of about 135 μm to about 325 μm depending on the selected flow rates. If monodisperse populations of microgels are required that are outside the 135-325 μm range, the microfluidic device nozzle can be scaled up or down so that nozzle is roughly equal to the desired microgel size.

In the Examples below, nozzle sizes of 200 μm, 300 μm, 400 μm, and 600 μm, were tested. The device used for islet encapsulation was scaled to have a 600 μm nozzle, and produced microgels from 300-800 μm in diameter. As a further demonstration of the versatility of this platform, human mesenchymal stem cells (hMSCs), were encapsulated in PEG-4MAL microgels of either 400 μm or 90 μm diameter, functionalized with a cell adhesive RGD peptide. After encapsulation, hMSCs encapsulated in both microgel sizes exhibited high viability, and hMSCs in 400 μm diameter microgels were maintained in suspension culture for 7 days with no loss in viability. Generally the nozzle size should between about 3 μm and 1,500 μm, or between about 50 μm and 1,000 μm, or between about 100 μm and 750 μm.

Droplet sizes can range from less than 10 μm to greater than 1,000 μm. The droplets can be monodispersed or polydispersed. In preferred embodiments, the droplets are monodispersed droplets of a size between about 10 μm and 1,000 μm, inclusive. In some embodiments, the droplets are of a size between about 100 μm and 400 μm, inclusive. In some embodiments, the droplets are of a size between about 10 μm and 20 μm, inclusive, or between about 15 μm and 20 μm, inclusive.

Flexibility in protein encapsulation, as well as the ability to simultaneously control therapeutic release kinetics and particle size, renders this encapsulation platform suitable for a wide range of cell and bioactive agent delivery applications.

III. Compositions for Making Microgels

A. Macromer Phase

The macromer phase typically includes a polymer or macromer and one or more cargos in an aqueous solution. The aqueous solution is typically a physiological buffer, for example, water, saline, buffered saline, etc. The buffer can be a nucleophilic buffer, such as triethanolamine (TEA).

1. Polymers

The marcomer phase includes a polymer or macromer. The polymer or macromer is one that can be crosslinked to form a microgel in the presence of a suitable crosslinker. Preferably, the polymer of the macromer phase is a hydrophilic multi-armed/branched macromer, as described in more detail below. The macromere can be formed from any of the suitable hydrophilic polymers provided herein or otherwise known in the art. In some embodiments, the molecular weight of the polymer or macromer is between about 1 and 200 kDa, or between about 1 and 100 kDa, or between about 1 and 50 kDa. For example, the polymer or macromer can have a molecular weight of "N" kDa, wherein N is any integer between 1 and 200. The polymer or macromer can have a molecular weight of "N" Da, wherein N is any integer between 1,000 and 200,000. In a particular embodiment, the molecular weight of the PEG or derivative thereof is "N" Da, wherein "N" is between 1,000 and 100,000, or between about 1,000 and 50,000.

Preferably, the polymer is a hydrophilic polymer. Exemplary macromers are known in the art. See, for example, U.S. Pat. No. 8,017,733, which provides a non-limiting list of water-soluble and non-peptidic polymers including polyalkylene glycol polymers, polyalkylene oxide homopolymers such as polypropylene glycols, polyoxyethylenated polyols, copolymers thereof and block copolymers thereof, as well as poly(oxyethylated polyol), poly(olefinic alcohol), poly(vinylpyrrolidone), poly(hydroxypropylmethacrylamide), poly (α-hydroxy acid), poly(vinyl alcohol), polyphosphazene, polyoxazoline, poly(N-acryloylmorpholine) and copolymers, terpolymers, and mixtures thereof.

A preferred polymer is ethylene glycol (EG) polymer (i.e., polyethylene glycol) (PEG) or a derivative thereof. Derivatives of PEG include, but are not limited to, methoxypolyethylene glycol succinimidyl propionate, methoxypolyethylene glycol N-hydroxysuccinimide, methoxypolyethylene glycol aldehyde, methoxypolyethylene glycol maleimide, PEG derivatives with "click" chemistries functional groups and multiple-branched polyethylene glycol.

The precise number of EG or derivative units depends on the desire porosity of the microgel, as discussed in more detail below. In some embodiments, the molecular weight of the PEG or derivative thereof is between about 1 and 200 kDa, or between about 1 and 100 kDa, or between about 1 and 50 kDa. For example, the PEG or derivative thereof can have a molecular weight of "N" kDa, wherein N is any integer between 1 and 200.

The PEG or derivative thereof can have a molecular weight of "N" Da, wherein N is any integer between 1,000 and 200,000. In a particular embodiment, the molecular weight of the PEG or derivative thereof is "N" Da, wherein "N" is between 1,000 and 50,000.

In specific exemplary embodiments, the PEG or derivative thereof is 10 kDa, 20 kDa, 30 kDa, 40 kDa, or 50 kDa.

In the most preferred embodiments, the polymer is a branched or multi-armed macromere with 2 or more "arms". In some embodiments, the macromer has between 2-8 arms, for example, 2, 3, 4, 6, or 8 arms. Multi-arm PEG, also referred to as "star" PEG, of various sizes are known in the art and commercially available.

In the most preferred embodiments, the polymer can be crosslinked by Michael-type addition reaction driven by the crosslinker. Therefore, in some embodiments, the polymer or macromer, for example PEG or derivative thereof, is modified to include a moiety that can facilitate crosslinking of two or more polymers by Michael-type addition. For example, moieties suitable for Michael-type addition include, but are not limited to, maleimides, vinyl sulfones, and acrylates. Other suitable reactive chemistries include N-hydroxysuccinimide, succinimidyl propionate, thiol-ene and other "click" chemistries.

In preferred embodiments, the polymer is PEG or derivative thereof including one or more maleimides. The maleimide(s) are typically linked to the end of the PEG polymer (see, for example FIG. 1). Also referred to herein as PEG-MAL, various maleimide-linked polyethylene glycol chains are known in the art. Such polymers are often used as flexible linking molecules to attach proteins to surfaces. The maleimide double bond readily reacts with a thiol group, for example the thiol group found on cysteine, to form a stable carbon-sulfur bond.

In the most preferred embodiments, the polymer is a maleimide-linked branched polyethylene glycol with 2 or more "arms". In some embodiments, the PEG, or derivative thereof, has between 2-8 arms, for example, 2, 3, 4, 6, or 8 arms. Multi-arm PEG, also be referred to as "star" PEG, of various sizes are known in the art and commercially available.

In a particular preferred embodiment, the polymer is a four arm PEG-MAL (also referred to herein as PEG-4MAL). The PEG-4MAL hydrogel system has advantages over other hydrogel chemistries, including a well-defined hydrogel structure, facile and stoichiometric incorporation of bioligands, increased cytocompatibility, improved crosslinking efficiency, and tunable reaction rates (Phelps, et al., *Advanced Materials*, 24(1):64-70 (2012)). Additionally, the PEG-4MAL macromer exhibits minimal toxicity and inflammation in vivo and is rapidly excreted via the urine (Phelps, et al., *Biomaterials*, 4602-11 (2013)), which indicate the polymers are likely to be well tolerated when used for the in vivo application disclosed herein.

2. Cargo

The macromer phase includes a cargo. The cargo is selected based on the desired application. The cargo is, or can include, proteins, peptides, amino acids, nucleic acids, carbohydrates, lipids, small molecules, or combinations thereof. In some preferred embodiments the cargo is a cell or cells, or a macromolecule such as a peptide or a protein.

a. Cells

The cargo can be a single cell. The cargo can be a group or cluster of cells. The cluster or group of cells can be homogenous (e.g., all of the same cell type), or heterogenous (e.g., two or more different cell types). Suitable cells include, but are not limited to differentiated mesenchymal cells, epithelial cells, neural cells, endothelial cells, epithelial cells, myoblasts, chondrocytes, myoblasts, osteoblasts, osteoclasts, bone marrow cells, adult stem cells, embryonic stem cells, umbilical cord blood cells, fibroblasts, or a combination thereof. In some embodiments, the cells are autologous or allogeneic cells. The autologous cells may be those naturally occurring in the donor or cells modified ex vivo. For example, in some embodiments, the cells have been recombinantly modified to contain one or more exogenous nucleic acids encoding desired protein products. In some embodiments, the cells are stem cells isolate from a donor and expanded and/or differentiated ex vivo prior to encapsulation.

In a particular embodiment, the cells are human pancreatic islets, for example, alpha cells, beta cells, delta cells, PP cells (gamma cells), epsilon cells, or any combination thereof.

In another particular embodiment, the cells are stem cells, for example mesenchymal stem cells (MSCs), bone marrow-derived stem cells, embryonic stem cells or induced pluripotent stem cells (iPSCs).

b. Bioactive Agents

In some embodiments, the cargo is one or more bioactive agent. The bioactive agents can small molecule active agents or biomacromolecules, such as proteins, polypeptides, or nucleic acids. Suitable small molecule active agents include organic and organometallic compounds. The small molecule active agents can be a hydrophilic, hydrophobic, or amphiphilic compound. The bioactive agent can be encapsulated within the microgel. The microgel can be porous enough to allow the bioactive agent to diffusion out to the microgel over time. Alternatively, in some embodiments, the microgel is not porous enough to allow the bioactive agent to diffuse out over time. For example, in some embodiments, the microgel encapsulates both cell(s) and one or more bioactive agents. The bioactive agent can be retained, encapsulated with the cells, thereby modulating the cells' microenvironment.

In some embodiment, the polymer is functionalized with one or more bioactive agents prior to crosslinking to form the microgel. In this way, small molecules, peptides, proteins, and other bioactive agents can be incorporated in the microgel. The active agents can be functionalized in such a way that they remain attached to the polymer, or such that they are later released from the microgel. For example, in particular embodiments the bioactive agent is functionalized in such a way that it can be released by a protease or other enzymes in vivo when administered to a subject in need thereof. The protease can be associated with a disease condition such that the bioactive agent is selectively released to treat the disease. For example, a therapeutic antibody or protein can be release by generating microgels crosslinked by molecules that can be cleaved by enzymes, such as cathepsins, metalloproteinases, and metalloproteases. In some embodiments, the bioactive agent is designed, engineered, functionalized or otherwise modified in include a proteolytic or other enzymatic cleavage site for one or more specific proteases or other enzymes.

In a particular embodiment, the polymer is a PEG-MAL such as PEG-4MAL, and the polymer is functionalized by reacting a bioactive agent with the maleimide group prior to crosslinking. The Examples below illustrate PEG-MAL functionalized with RGD peptide. The peptide remained bound to the polymer and supported cell adhesion, survival, and function.

Exemplary bioactive agents include tumor antigens, CD4+ T-cell epitopes, cytokines, chemotherapeutic agents, radionuclides, small molecule signal transduction inhibitors, photothermal antennas, immunologic danger signaling molecules, other immunotherapeutics, enzymes, antibiotics, antivirals, anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, immunomodulators (including ligands that bind to Toll-Like Receptors (including but not limited to CpG oligonucleotides), nutraceuticals such as vitamins, and oligonucleotide drugs (including DNA, RNAs, antisense, aptamers, small interfering RNAs, ribozymes, external guide sequences for ribonuclease P, and triplex forming agents).

Bioactive agents can be diagnostic agents, for example, paramagnetic molecules, fluorescent compounds, magnetic molecules, and radionuclides, x-ray imaging agents, and contrast agents.

Bioactive agents can be immunomodulatory such as cytokines, xanthines, interleukins such as interleukin-2 and -3, interferons including interferon-alpha, -beta and -gamma, oligodeoxynucleotides, glucans, growth factors (e.g., TNF, CSF, GM-CSF, G-CSF, bFGF(FGF-1), aFGF(FGF-2), EGF (epidermal growth factor), PDGF (platelet-derived growth factor), IGF (insulin-like growth factor), TGF-β1 through 3, including the TGF-β superfamily (BMPs, GDF-5, ADMP-1 and dpp)), hormones such as estrogens (diethylstilbestrol, estradiol), androgens (testosterone, HALOTESTIN® (fluoxymesterone)), progestins (MEGACE® (megestrol acetate), PROVERA® (medroxyprogesterone acetate)), and corticosteroids (prednisone, dexamethasone, hydrocortisone).

In some embodiments, the bioactive agent is a hormone, such as, insulin, growth hormone-releasing factor and calcitonin. The hormone can be non-peptide hormone.

The cargo can also be antigens and/or adjuvants (i.e., molecules enhancing an immune response), or other peptide, protein, or DNA based vaccines components.

In a preferred embodiment, the cargo includes one or more growth factors. Growth factors include, but are not limited to adrenomedullin (AM), angiopoietin (Ang), autocrine motility factor, bone morphogenetic proteins (BMPs), brain-derived neurotrophic factor (BDNF), epidermal growth factor (EGF), erythropoietin (EPO), fibroblast growth factor (FGF), glial cell line-derived neurotrophic factor (GDNF), granulocyte colony-stimulating factor (G-CSF), granulocyte macrophage colony-stimulating factor (GM-CSF), growth differentiation factor-9 (GDF9), healing factor, hepatocyte growth factor (HGF), hepatoma-derived growth factor (HDGF), insulin-like growth factor (IGF), keratinocyte growth factor (KGF), migration-stimulating factor, myostatin (GDF-8), nerve growth factor (NGF) and other neurotrophins, platelet-derived growth factor (PDGF), thrombopoietin (TPO), transforming growth factor alpha(TGF-α), transforming growth factor beta(TGF-β), tumor necrosis factor-alpha(TNF-α), vascular endothelial growth factor (VEGF), Wnt and Wnt Signaling Pathway molecules, placental growth factor (PGF), [(Foetal Bovine Somatotrophin)] (FBS), IL-1-Cofactor for IL-3 and IL-6, IL-2, IL-3, IL-4, IL-5, IL-6, and IL-7.

In a preferred embodiment, the cargo includes one or more chemokines Chemokines including, but not limited to CC chemokines, CXC chemokines, C chemokines, and CXC3 chemokines CC chemokines include: CCL1, CCL2, CCL3, CCL4, CCL5, CCL6, CCL7, CCL8, CCL9/CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28. CXC chemokines include: CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, and CXCL17. C chemokines include: XCL1 and XCL2. CXC3 chemokines include CX3CL1.

In some embodiments, the agents are those factors, proteinaceous or otherwise, which are found to play a role in the induction or conduction of growth of bone, ligaments, cartilage or other tissues associated with bone or joints, such as for example, BMP and bFGF.

B. Shielding/Oil Phase

The oil phase (also referred to herein as the shielding phase) is composed of oil and surfactant. In preferred embodiments, the oil is mineral oil. Other suitable oils include, but are not limited to, propylene glycol, glycerol, and vegetable oil. In a preferred embodiment, the surfactant is SPAN® 80 (e.g., 2%, as exemplified in the Examples below). Other suitable surfactants are known in the art. A non-limiting list of preferred surfactants includes, TWEEN®-80, polysorbate-20, polysorbate-80, and ammonium lauryl sulfate, among others. The surfactant concentration typically ranges from about 0.1% to about 20%.

C. Crosslinker Phase

The crosslinker phase is generally constitutionally similar to the oil phase and further including a crosslinker capable of crosslinking the polymer in the macromer phase to form a microgel. As droplets containing cargo are formed, diffusion of the crosslinker from the crosslinker phase crosslinks the hydrogel network, forming a semipermeable capsule. While some crosslinkers can be dissolved directly in a continuous phase (oil phase) to form the crosslinker phase, hydrophilic chemicals are first dissolved in aqueous phase to form a crosslinker-in-oil emulsion. In the Examples below, the crosslinker phase is composed of the continuous phase (oil phase) with an emulsion of the crosslinker. However, it will be appreciated that the oil and surfactant components and/or percentages of the crosslinker phase need not be exactly the same as the components and/or percentages of the oil phase. More specifically, in some embodiments, the oil phase and crosslinker phase are composed of the same oil and in the same surfactant. In some embodiments, the oil phase and crosslinker phase are composed of the same oil and different surfactants. In some embodiments, the oil phase and crosslinker phase are composed of different oils and the same surfactant. In some embodiments, the oil phase and crosslinker phase are composed of different oils and different surfactants. The percent of the surfactant in the oil and crosslinker phases can be same, or can be different.

The crosslinker is ultimately selected based on the polymer being used to form the microgel. Preferably the crosslinker is cytocompatibe and is not toxic to cells. In the most preferred embodiments, the crosslinker cause little or no cell death, and/or little or no cell stress when cells are encapsulated according to the disclosed platform.

In the most preferred embodiment, the polymer includes one or more moieties that enable its crosslinking to other polymer molecules via a Michael-type addition reaction between the polymer/macromer and crosslinker. In a particular embodiment, the polymer/macromer includes one or more maleimide groups, the crosslinker includes one or more thiols, and the Michael-type addition reaction is between the maleimide groups on the polymer/macromer and thiols on the crosslinker. Fast reaction kinetics renders this hydrogel advantageous for microfluidic encapsulation, allowing for short residence time on chip, and minimizing cell stress. This Michael-type addition reaction requires no free radicals and is cytocompatible (Phelps, et al., *Advanced Materials,* 24(1): 64-70 (2012)). The Examples below show that a microencapsulation process carried out in this way does not affect the viability or function of human pancreatic islets and mesenchymal stem cells (hMSCs).

Exemplary crosslinkers include dithiothreitol (DTT) and biodegradable crosslinkers, for example, cysteine-containing peptides such

| Biodegradable crosslinkers | Peptide sequence | Mw |
|---|---|---|
| GPQ (W) (SEQ ID NO: 2) | GCRDGPQGIWGQDRCG (SEQ ID NO: 4) | 1704.88 |
| VPM | GCRDVPMSMRGGDRCG (SEQ ID NO: 5) | 1696.99 |
| GPQ (A) (SEQ ID NO: 3) | GCRDGPQGIAGQDRCG (SEQ ID NO: 6) | 1589.74 | which are examplifed in the Examples below and described in Phelps, et al., *Biomaterials,* 34(19):4602-4611 (2013). Such peptide typically include at least one, preferably two or more cysteines. In addition to DTT and cysteine(s)-containing peptides, other molecules containing free thiols, including functionalized carbohydrates and nucleic acids, can be used.

In some embodiments, the crosslinker is designed to be degraded in the presence of a protease or another enzyme or molecule. Such embodiments can be designed to fine tune the release of the cargo by degrading the microgel. For example, in some embodiments, the crosslinker is designed to be degraded over time in vivo in the presence of a protease or another enzyme or molecule that is expressed in vivo. In other embodiment, protease or another enzyme or molecule can be provided (for example administered to the subject) to facilitate release of the cargo. In some embodiments, expression or presence of the protease, or other enzyme or molecule is correlated with a disease or disorder so that cargo is released preferential under disease conditions or in close proximity to a diseased area. In a particular embodiment, the crosslinker is a peptide that includes one or more cysteines that can crosslink macromers by a Michael-type addition reaction, but also includes a proteolytic site for one or more enzymes. In the most preferred embodiments, the peptide includes a cleavage site and least one cysteine on each side of the cleavage site. Examples include, but are not limited to, the biodegradable crosslinkers discussed above, and in the Examples below, which can be degraded by a wide range of proteases including collagenase I (e.g., cysteine-flanked protease-degradable peptide GCRDVPMS↓MRGGDRCG (SEQ ID NO:5) (VPM), where ↓ indicates the cleavage point). Exemplary peptide crosslinkers include, but are not limited to, peptides including the amino acids of SEQ ID NOS:4, 5, or 6, or a variant thereof with at least 70%, 80%, 85%, 90%, 95%, or more sequence identity to SEQ ID NO:4, 5, or 6, and which preferably includes two cysteines, and can be cleaved by one or more proteases.

As discussed in more detail above and exemplified below, this system is also easily modified with thiol-containing molecules, including cysteine-containing adhesive ligands and growth factors and other bioactive agents, due to the high specificity of the maleimide groups for thiols at physiological pH.

In the most preferred embodiments, the crosslinking is not based on ultraviolet (UV) initiated photopolymerization and/or free radical generation.

IV. Methods of Using Microgels

The microgels disclosed herein can be utilized in a number of in vivo applications. Exemplary applications include cell transplantation and drug delivery.

A. Transplantation

Encapsulated cells produced according to the present disclosure can be transplanted into subjects as a treatment of pathologies including, but not limited to tissue damage, ischemia, insulin-dependent diabetes, heart attack, nerve damage, brain damage, bone damage, or cartilage repair. Such transplantation may be into the peritoneal cavity of the subject, or directly into a pathology site.

The methods can be used to generate cells which may be useful in the treatment of a variety of diseases and disorders, including, but not limited to, neurodegenerative diseases such as Parkinson's, Alzheimer disease, and multiple sclerosis. The methods are also useful for organ regeneration, and for restoration or supplementation of the immune system. For example, cells at different stages of differentiation such as iPS cells, hematopoietic stem cells, multipotent cells or unipotent cells such as precursor cells, for example, epithelial precursor cells, and others can be administered intravenously or by local surgery to treat a disease or disorder. In some embodiments, the droplets are designed to direct cell behavior and fate of encapsulated cells, cell adjacent to the site of implantation, or a combination thereof. The methods can be used in combination with other conventional methods, such as a prescription medication regime, surgery, hormone therapy, chemotherapy and/or radiotherapy.

In some embodiments, the microgel is designed to be immunoisolated from the host tissue. The permeability or porosity of microgel can be fined tuned according to the methods disclosure herein to be selective permeability, for example, prevented antibodies and immune cells (relatively large objects) from reaching encapsulated cells, while nutrients, signaling molecules, and waste (relatively small molecules) can be easily transported across the microgel capsule. In this way the transplanted cells can carry out their purpose will evading detection and rejection by the host's immune system.

The encapsulated cells can be implanted or injected directly into the site as needed. Microgel droplets having a diameter greater than 250 µm may tend to block needles used to deliver the droplets to a host. Accordingly, the disclosed microcapsules having a diameter of less than about 250 µm, typically less than about 200 µm can be delivered to a host via injection with a standard surgical needle, for example a 14 gauge or 18 gauge needle, in an amount sufficient to treat the host. Large microgel droplets may be delivered using a larger needle or an alternative approach, for example, surgical implantation.

The encapsulated cells can be cells that secrete a polypeptide needed to treat the pathology, for example insulin to control glycemia. It will be apparent to those skilled in the art that the quantity of microgel droplets transplanted depends on the ability of the microgel droplets to provide function in vivo. One skilled in the art will be able to determine suitable transplantation quantities of microgel droplets, using techniques as are known in the art.

A further embodiment provides a method for treating a host by delivering encapsulated cells to the host produced according to the present disclosure. For example, the encapsulated cells can produce cartilage or cartilage components, or secrete insulin in the host.

A further embodiment provides a method for repairing tissue in a host by administering encapsulated cells produced according the present disclosure, wherein the encapsulated cells produce tissue or tissue components in the host.

B. Drug Delivery

In some embodiments, the microgel droplets do not contain cells. In such embodiments the microgel droplets are typically loaded with or functionalized with a bioactive agent such as those discussed above. The microgel droplets can be used to deliver an effective amount of one or more therapeutic, diagnostic, and/or prophylactic agents to an individual in need of such treatment. The amount of agent to be administered can be readily determine by the prescribing physician and is dependent on the age and weight of the patient and the disease or disorder to be treated.

The microgel droplets are useful in drug delivery (as used herein "drug" includes therapeutic, nutritional, diagnostic and prophylactic agents), whether injected or surgically administered. The microgel droplets are typically administered in an aqueous suspension (in water, saline, buffered saline, etc.).

As discussed herein, microgel droplets can be used to as delivery vehicles for a number of active agent cargos including small molecules, nucleic acids, proteins, and other bioactive agents. The active agent or agents can be encapsulated within, dispersed within, and/or associated with the surface of the microgel. In some embodiments, the microgel packages two, three, four, or more different active agents for simultaneous delivery.

The release kinetics of the cargo can be modulated by varying the permeability of the microgel as discussed in more detail above. Therefore, depending on the size of the agent and the permeability of the microgel, the microgel formulation can be designed for immediate release (e.g., burst release), or slow or extended release over time.

The active agent-loaded microgel droplets can be used to treat a variety of diseases and conditions, for example, cancer and infectious diseases. The compositions can be administered to the subject therapeutically or prophylactically.

C. Pharmaceutical Compositions

Pharmaceutical compositions including microgel droplets are provided. Pharmaceutical compositions can be for administration by transplantation, parenteral (intramuscular, intraperitoneal, intravenous (IV) or subcutaneous) injection, or another suitable means. Compositions can be formulated in dosage forms appropriate for each route of administration.

In some embodiments, the compositions are administered systemically, for example, by intravenous or intraperitoneal administration, in an amount effective for delivery of the compositions to targeted cells, tissue, etc.

In certain embodiments, the compositions are administered locally, for example by transplantation or injection directly into a site to be treated. In some embodiments, the compositions are injected or otherwise administered directly diseased or disorder tissue. Typically, local injection causes an increased localized concentration of the compositions which is greater than that which can be achieved by systemic administration. In some embodiments, the compositions are delivered locally to the appropriate cells by using a catheter or syringe. Other means of delivering such compositions locally to cells and tissue include using infusion pumps (for example, from Alza Corporation, Palo Alto, Calif.) or incorporating the compositions into implants.

The microgels can be formulated in a physiologically acceptable carrier or vehicle, and injected or otherwise delivered into a tissue or fluid surrounding the target area.

As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired.

In a preferred embodiment the nanolipogels are in a pharmaceutical composition including an aqueous solution suitable for parenteral delivery. The formulation can be in the form of a suspension or emulsion. In general, pharmaceutical compositions are provided including effective amounts of cargo, and optionally include pharmaceutically acceptable diluents, preservatives, solubilizers, emulsifiers, adjuvants and/or carriers. Such compositions can include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. Optional components of a pharmaceutical composition can be selected based on the composition of the microgel and its cargo. For example, if the cargo is cells, the additional agents in the pharmaceutical composition should be compatible with cell viability.

EXAMPLES

Example 1

Design and Testing of a Microfluidic Strategy for Encapsulating Cells and Other Biological Agents Materials and Methods Microfluidic Device Preparation PDMS microfluidic flow focusing devices were cast using soft lithography from silicon and SU8 masters that were fabricated by the Stanford Microfluidics Foundry. Devices with 300 µm nozzles were bonded directly to glass slides after treatment with air plasma. 600 µm nozzle devices were manufactured by first bonding mirror-image PDMS channels, each with 300 µm depth, together to create a channel with 600 µm depth.

PEG-4MAL Microgel Formation and Particle Encapsulation

Flow-focusing microfluidic geometry was utilized to form polymer droplets. Both shielding and crosslinker phases consisted of light mineral oil (Sigma) with 2% SPAN80 (Sigma). The crosslinker phase also contained an emulsion, at a ratio of 1:15, of 20 mg/mL dithiothreitol (DTT) (Sigma) in PBS. A co-flowing shielding phase protected the macromer solution—a 5% PEG-4MAL (10 kDa or 20 kDa, Laysan Bio) solution containing molecules or cells to be encapsulated—from the crosslinker phase until droplets of the macromer solution were formed. DTT rapidly diffused into macromer droplets, forming crosslinked microgels. To functionalize hydrogel with GRGDSPC (SEQ ID NO:1) ('RGD', AAPPTec), macromer was reacted for 20 minutes before encapsulation with 2.0 mM RGD in buffer solution containing 4 mM triethanolamine (Sigma). After formation, microgels were washed 5 times by centrifugation to remove mineral oil and excess DTT.

Results

FIG. 1 illustrates a platform and strategy to produce cell- and cell aggregate-laden synthetic PEG-4MAL-based microgels, functionalized with cell adhesive peptides, by producing droplets using a flow focusing microfluidic device and subsequently covalently crosslinking the droplets with the small molecule dithiothreitol (DTT). Three independent flows of (1) mineral oil containing SPAN80 (a surfactant), (2) a crosslinker phase containing mineral oil and SPAN80 with an emulsion of aqueous DTT solution, and (3) PEG-4MAL macromer in aqueous physiological buffer were pumped into the microfluidic chip using syringe pumps. As the macromer phase approached the flow-focusing nozzle, a coflowing continuous phase of oil shielded the macromer from contact with the crosslinker-laden oil phase. Because crosslinker could not reach the macromer before flow instability occurred, monodisperse, spherical droplets were formed. The crosslinker then rapidly diffused into droplets, covalently crosslinking the PEG-4MAL macromer into the microgel network via Michael-type addition reaction of the maleimide groups on the macromer and thiols on the crosslinker. The PEG-4MAL hydrogel platform used for this system is easily modified with thiol-containing molecules, including cysteine-containing adhesive ligands and growth factors, due to the high specificity of the maleimide groups for thiols at physiological pH.

This Michael-type addition reaction requires no free radicals and is cytocompatible (Phelps, et al., *Advanced Materials*, 24(1):64-70 (2012)). Furthermore, fast reaction kinetics render this hydrogel ideal for microfluidic encapsulation, allowing for short residence time on chip, and minimizing cell stress.

Example 2

Size and Dispersity of the Microgels are Tunable
Materials and Methods

Microgel Size Control

To characterize the relationship between microgel size and the various macromer solution and continuous phase flow rates, hydrogel droplets were generated using computer-controlled syringe pumps, and were measured while still in the microfluidic chip. Harvard Apparatus Elite syringe pumps were computer controlled using FlowControl software to pump inlet solutions at various flow rates. Video was recorded during droplet generation using a Hammamatsu ORCA-ERA 1394 camera connected to a Nikon TE300 microscope. Droplet diameter was measured using ImageJ analysis software. The coefficient of variation (CV) was calculated for each flow rate combination by dividing the standard deviation of the sample by its mean. At least 30 microgels were measured for each flow rate combination.

Results

Precise control of particle size and monodispersity are critical for many applications of microgels, and the microfluidic platform affords this control over a wide range of particle sizes. The macromer solution and continuous phase flow rates for a device with a 300 μm nozzle, were varied and corresponding droplet size for each flow rate was measured (FIG. 2A-2E). No cells were encapsulated in this application. Microgels with a wide range of sizes, ranging from 20 to 400 μm, could be produced on the same device; however, several flow regimes produced microgels with undesirable polydisperse distributions (coefficient of variation, CV>10%).

Importantly, flow rate combinations were identified that produced a range of microgel sizes from 135-325 μm with monodisperse populations (CV<5%). An example of one of these flow rates is shown in FIGS. 2A-2E, along with several other representative flow regimes, including one regime that does not produce droplets and one that produces a very polydisperse (CV=22%) microgel population. Although a device with fixed geometry is capable of producing a wide range of particle sizes, preferably droplets should be generated with diameters that are 50-100% of the nozzle width to obtain a monodisperse population. Even if polydisperse populations are acceptable, device throughput is limited, because no droplets were formed for any PEG-4MAL macromer flow rates exceeding 50 μL min-1. If monodisperse populations of microgels are required that are outside the 135-325 μm range, the microfluidic device nozzle can be scaled up or down so that nozzle is roughly equal to the desired microgel size.

Example 3

Permeability of the Microgels is Tunable

Materials and Methods

Protein Encapsulation and Release

AlexaFluor488-labeled IgG (goat anti-rabbit IgG, Life Technologies), bovine serum albumin-AlexaFluor488 conjugate (Life Technologies), 2-NBDglucose (Life Technologies) or insulin (Sigma) tagged with AlexaFluor488 was dissolved in a 5% PEG-4MAL (10 kDa or 20 kDa) solution before being microencapsulated by macromere droplet gelation. To prevent proteins from being crosslinked by the macromer, thiols were capped using aminoethylate reagent (Thermo Scientific) according to product instructions. Particles were washed and resuspended in PBS and divided into 5 replicates containing 2 mL total volume. 50 μL samples were taken of supernatant alone, as well as of supernatant containing well-mixed, protein-laden microgels. These samples were placed in a 96 well plate, and their fluorescent intensity was measured using a Perkin Elmer HTS 7000 plate reader. To generate release curves, supernatant samples were collected over the course of 3 days, and their fluorescent intensity was measured. Protein release was normalized by setting fluorescent intensity of the supernatant alone correspond to 0% protein released, and fluorescent intensity of the buffer/microgel mixture correspond to 100% protein released. This data was plotted using GraphPad Prism, and exponential best fit curves were calculated from normalized data.

Results

Figure 3A:
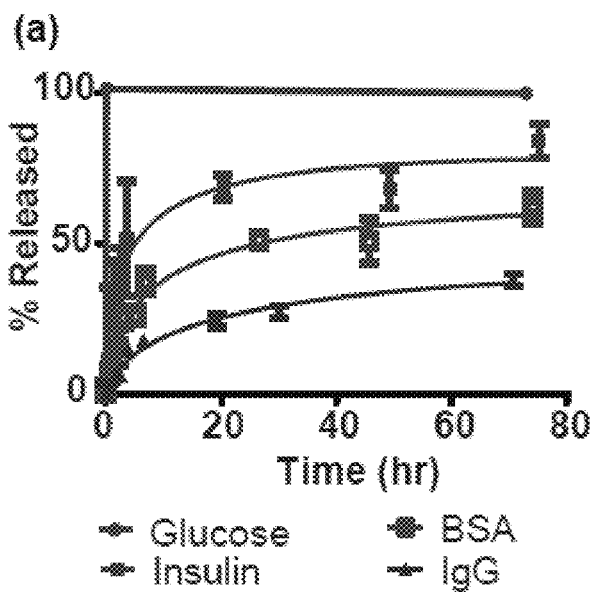
FIG. 3A is a line graph showing the release kinetics (% release) for biomolecules of varying size (glucose, insulin, BSA, IgG) from microgels (made with 20 kDa macromers).

A tunable hydrogel network with selective permeability to biomolecules is important for cell microencapsulation, because antibodies and immune cells (relatively large objects) must be prevented from reaching encapsulated cells, while nutrients, signaling molecules, and waste (relatively small molecules) should be easily transported across the microgel capsule. Therefore, the suitability of microgels for biomolecule release and cell encapsulation was tested by measuring their permeability to relevant molecules of various sizes that were labeled with fluorescent tags. These molecules were encapsulated within microgels generated from a 20 kDa PEG-4MAL macromer, and the rate of their release into buffer was used as a metric of permeability (FIG. 3A).

2-NBD-glucose (342 Da) was rapidly released from the gels, fully equilibrating concentration with the buffer by the first fluorescence measurement, 5 minutes after swelling. Similarly, insulin-AlexaFluor488 (5.8 kDa) was rapidly released from the microgels upon swelling, indicating that relevant functional molecules diffuse quickly through the microgel.

In contrast, encapsulated IgG-AF488 (~160 kDa) was released from the microgels at a slow rate, indicating that the microgel capsules are capable of preventing transport and binding of antibodies to encapsulated cells. Release kinetics for BSA (66.5 kDa) fell between IgG and insulin, indicating that physical molecular entanglement due to the network structure is the determining factor for permeability in our hydrogel network. These results show nearly 100% release for the smaller molecules glucose and insulin. For the larger proteins BSA and IgG, the release did not reach 50% of the incorporated amount because these larger molecules remain trapped within the tight network structure of the PEG hydrogel.

Figure 3B:
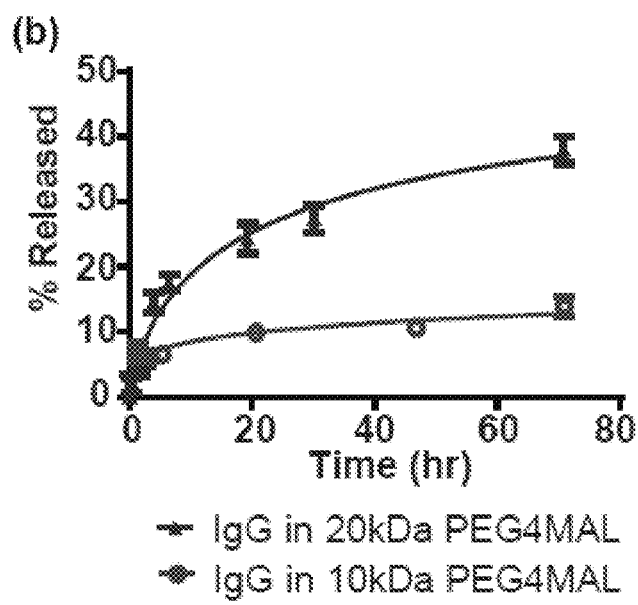
FIG. 3B is a line graph showing the % release of IgG from microgels made with 20 kDa macromers verses the % release of IgG from microgels made with 10 kDa.

These results for reduced transport and entrapment of IgG support the use of these materials for immuno-encapsulation applications. As a demonstration of the ability to tune network structure for protein release applications, IgG was encapsulated in microgels made with PEG macromers of different (10 kDa vs. 20 kDa) molecular weights (FIG. 3B). The tighter network mesh of the microgels based on 10 kDa macromers slowed the release of IgG compared to microgels made with 20 kDa macromer.

Because altering macromer size results in drastic changes in release kinetics, it is believed that other parameters that influence network structure as related to the hydrogel correlation length, such as polymer weight % and crosslinking density, can be systematically varied to obtain desired release kinetics. Flexibility in protein encapsulation, as well as the ability to simultaneously control therapeutic release kinetics and particle size, indicate that this encapsulation platform is useful for a wide range of protein delivery applications.

Example 4

Microgels can Encapsulate Clusters of Cells

Materials and Methods

Human MSC Encapsulation and Viability Assay

Passage 3 hMSCs (Texas A&M Health Science Center College of Medicine) were trypsinized and washed 3 times with PBS before being suspended in RGD-functionalized macromer solution (5% wt macromer) at a concentration of $5 \times 10^6$ cells/mL. Generation and subsequent gelation of cell-laden macromere solution droplets, using a microfluidic device with a 300 μm nozzle, resulted in microencapsulated hMSCs. These cells were maintained under static culture conditions in chemically defined MSC media (Lonza) for 7 days, with media changes every 2 days. On days 1, 2, 3, 4, and 7, microencapsulated cells were removed from culture, stained with Calcein AM and TOTO-3 iodide (Life Technologies) for 15 minutes, washed, and resuspended in fresh media. At least 200 cells were imaged each day using a Nikon Eclipse Ti microscope, and their viabilities were assessed based on fluorescent signal. ANOVA analysis was performed using GraphPad Prism software. The percent viability was calculated by taking the ratio of live cells to total cells. Viability data was plotted using GraphPad Prism. ANOVA analysis between the groups found no significant difference in viability, and a student's t-test between days 1 and 7 also found no significant difference in viability.

Human Islet Encapsulation and In Vitro Characterization

Human pancreatic islets (PRODO Laboratories and the Integrated Islet Distribution Program) were suspended at a concentration of $2 \times 10^4$ IEQ/mL in culture media containing 5% (w/v) macromer. A microfluidic device with a 600 μm nozzle was used for droplet generation and subsequent crosslinking of the macromer solution, resulting in microencapsulated islets. After microencapsulation, islets were washed 5 times with media (PRODO labs PIM(S)), placed in fresh media, and allowed to recover overnight. On days 1, 2, 5, and 8 after encapsulation, islets were stained with Calcein AM and TOTO-3 iodide (Life Technologies) for 15 minutes, washed, and resuspended in fresh media. At least 74 islets were imaged each day using a Nikon Eclipse Ti microscope, and their viabilities were assessed based on fluorescent signal. For each islet, dead cell area to total islet area was computed, and this fraction was subtracted from 100% to obtain percent viability. ANOVA analysis was performed using GraphPad Prism software, and no significant difference in viability was found.

On day 1 following encapsulation, a glucose-stimulated insulin secretion assay was performed. Islets were washed and were equilibrated using 1.67 mM glucose in Hanks Buffered Salt Solution for 30 minutes. Two groups, containing 5 replicates of approximately 10 islets each, were collected from both microencapsulated and bare islets. One group from each treatment was incubated with high (16.7 mM) glucose HBSS, and the other group was incubated with low (1.67 mM) glucose HBSS for one hour. Supernatant from each sample was collected, and insulin content was quantified using human insulin ELISA (Sigma). DNA from each sample was then quantified using a Quant-iT PicoGreen kit (Invitrogen). Insulin secretion was normalized to DNA content for each well. The Stimulation Index for each replicate was calculated by taking the ratio of normalized high glucose insulin secretion to normalized low glucose insulin secretion (n=5). Groups were compared using a student's t-test in GraphPad Prism. Human islets and MSCs were obtained by third party distributors, and consent was provided by donors or next of kin.

Results

Having shown the ability to exclude high molecular weight proteins such as IgG with minimal impact on the transport of critical molecules such as glucose and insulin, cell encapsulation applications of this microgel system were examined using clinically relevant cell types. Human pancreatic islets were encapsulated with high efficiency (>99% of islets loaded into microfluidic device were encapsulated, and 80% of microgels produced contain at least one islet), in microgels made from PEG-4MAL, a polymer that has been shown to support islet engraftment and function (Phelps, et al., *Biomaterials*, 4602-11 (2013)).

Encapsulated islets were maintained in culture for 8 days with no decrease in viability (FIG. 3C-3D), demonstrating the capacity of this synthetic hydrogel network to support high viability of these sensitive human cells. This result also shows that any potentially cytotoxic effects of hydrogel precursor constituents (e.g., DTT) prior to network formation are mitigated by the short residence time of cells in crosslinker emulsion.

Figures 3C, 3D, 3E, 3F, 3G:
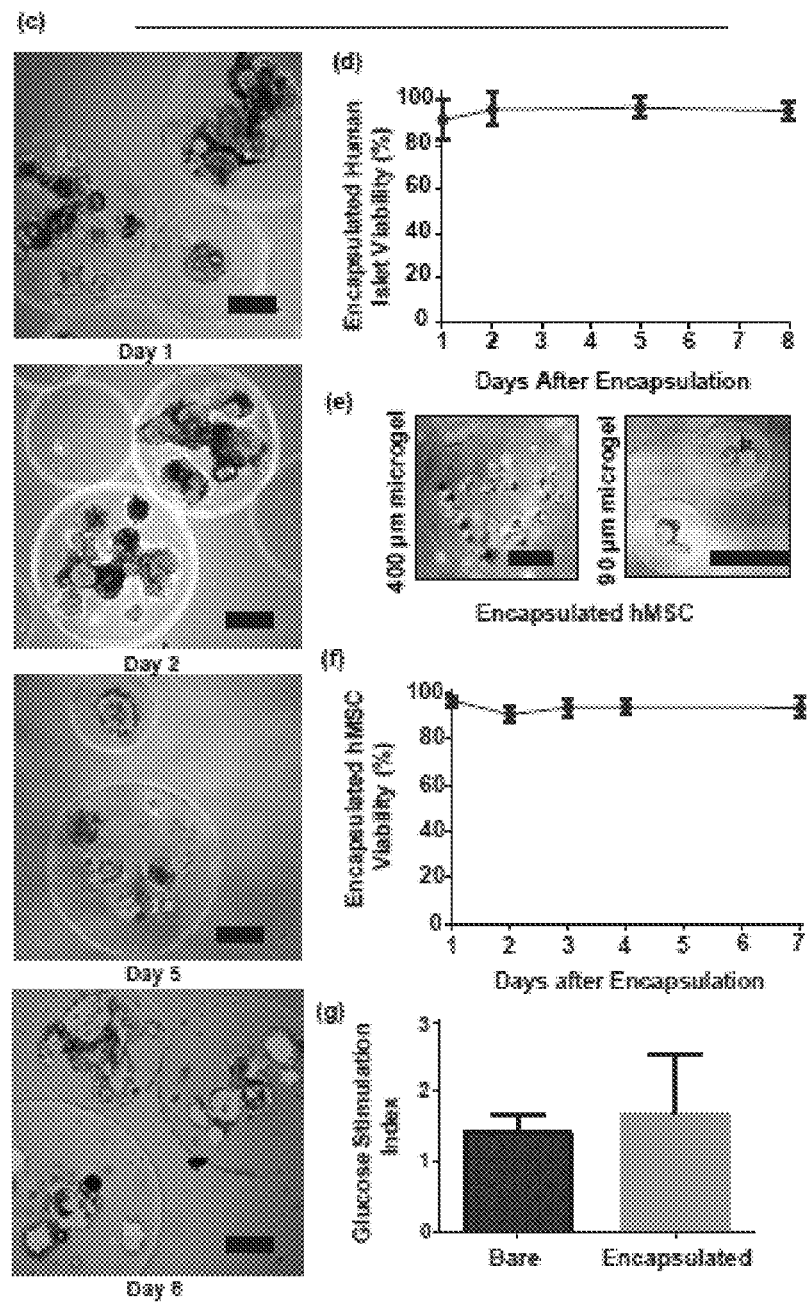
FIG. 3C is a series of representative pictomicrograph showing human islets in culture after encapsulation (days 1, 2, 5, and 8 after microencapsulation) (scale bars=200 μm).
FIG. 3D is a line graph showing the viability of human islets in culture 1, 2, 5, and 8 after microencapsulation, quantified using fluorescent area ratios between TOTO-3 iodide (dead) and calcein AM (live).
FIG. 3E is a series of representative pictomicrograph showing human mesenchymal stem cells (hMSC) that were encapsulated in microgels of various sizes (scale bars=100 μm).
FIG. 3F is a line graph showing the viability of hMSC in culture 1, 2, 3, 4, and 8 after microencapsulation in 400 μm microgels.
FIG. 3G is a bar graph showing the glucose stimulation index measured by a glucose stimulated insulin secretion assay for bare and microencapsulated cells one day after human islet encapsulation.

The device used for islet encapsulation was scaled to have a 600 μm nozzle, and produced microgels from 300-800 μm in diameter. As a further demonstration of the versatility of this platform, human mesenchymal stem cells (hMSCs), currently under investigation for various biomedical applications due to their regenerative and immunomodulatory properties, were encapsulated in PEG-4MAL microgels of either 400 μm or 90 μm diameter. These microgels were precisely functionalized with a cell adhesive RGD peptide (2.0 mM) by simply reacting maleimide groups in the macromer with this peptide prior to cell encapsulation and hydrogel crosslinking. This RGD peptide supports cell adhesion, survival and function when incorporated into the PEG-4MAL network (Phelps, et al., *Advanced Materials*, 24(1):64-70 (2012)). After encapsulation, hMSCs encapsulated in both microgel sizes exhibited high viability (FIG. 3E), and hMSCs in 400 μm diameter microgels were maintained in suspension culture for 7 days with no loss in viability (FIG. 3F). Therefore, controlled presentation of adhesive peptides to cells encapsulated using a cytocompatible crosslinking reaction provides an environment amenable to long-term cell viability. Such a microenvironment presenting defined bioactive peptides may be suitable not only for cell encapsulation and delivery (Ranganath, et al., *Cell Stem Cell*, 10(3):244-58 (2012)), but also for directing stem cell behavior and fate (Lutolf, et al., *Nature*, 462(7272):433-41 (2009), Lienemann, et al., *Advanced Healthcare Materials*, 2(2):292-6 (2013)). Additionally, control of microgel size facilitates optimization for cell delivery applications.

An important consideration in the engineering of microgels for cell encapsulation is that key cell functions are not negatively impacted following encapsulation. To this end, a glucose-stimulated insulin secretion (GSIS) assay was carried out to evaluate the function of encapsulated human islets. Bare or encapsulated islets were challenged with either 1.67 mM or 16.7 mM glucose for 30 minutes, and the normalized insulin content from each group was assayed using ELISA. The stimulation index (SI), or ratio of normalized insulin secreted in high glucose group to that of low glucose group, was calculated for both bare and encapsulated islets. No significant difference was found between the groups (FIG. 3F), demonstrating that microfluidic-based encapsulation in PEG-4MAL has no deleterious effects on human islet function or viability, and that mass transfer of molecules relevant to islet function is not significantly affected by microencapsulation.

The high potential of synthetic hydrogel microencapsulation for cell and protein therapeutics has been limited by the lack of synthetic polymer systems with tunable capsule size, cytocompatible crosslinking reactions, rapid crosslinking rates, adequate biomolecule permeability, and ease of functionalization with bioactive molecules (e.g., adhesive peptides). Using a synthetic hydrogel system with tunable network and crosslinking characteristics and a microfluidics encapsulation platform, an integrated and robust strategy for microencapsulation of cells with tunable capsule size and local cellular microenvironment was created. Additionally, microgel network structure can be modulated to affect the permeability of the capsule to molecules of various sizes.

Example 5

Cell Performance can be Modulated by Altering Encapsulation Dynamics

Initial microfluidic device prototypes featuring a 600 μm diameter liquid phase extrusion needle produced hydrogel capsules on the scale of the smallest capsules produced with established and traditional methods (200-600 μm). Subsequent prototype designs featuring a 400 μm diameter extrusion needle produced capsules in the range of 50-300 μm, which produces minimal void space and is the preferred for the application of islet encapsulation. Examples of islet-containing capsules generated with both devices exhibited reduction in capsule size is evident, as well as a reduction in the number of islets contained per capsule (600 μm device relative to 400 μm devise).

For some embodiments, for example pancreatic islet microencapsulation for immunoisolation, it may be desirable to have smaller capsule sizes. The system was modulated to reduce capsule size to ~300 μm without increasing incidence of microfluidic channel clogging by utilizing a flow focusing device with a 400 μm nozzle.

Figure 4A:
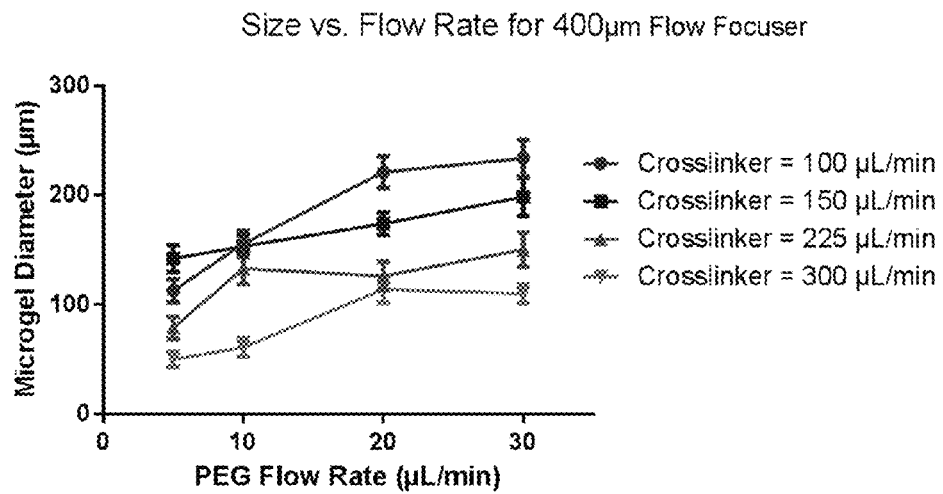
FIG. 4A is a line graph showing the microgel diameter (μm) as a function of PEG flow rate (μl/min) for various crosslinker flow rates (100, 150, 225, 300 μl/min).

Characterization of microgel size vs inlet flow rates is illustrated in FIG. 4A. Utilizing flow rates that produce capsules below 200 μm for islet encapsulation results in sporadic encapsulation of islets, because islets are excluded from capsules when flow is focused to dimensions smaller than islet size.

Smaller device dimensions allow for production of smaller microgels for islet encapsulation. Attempts at single cell encapsulation utilizing the platform were also successful. Single cells can be encapsulated in ~50 μm capsules with low polydispersity if very dilute cell suspensions are used for encapsulation. However, cell throughput is can be compromised under these conditions, leading to large numbers of empty capsules. At higher cell densities, however, satisfactory cell throughput is obtained (approximately 5E5-1E6 cells per second). Although some cells remain unencapsulated, and some increase in capsule polydispersity is noted, most capsules containing cells have around 5-15 cells, and capsule size ranges from 40-100 μm.

It is believed that cell ordering channels will further increase the efficiency of single cell encapsulation. This feature can be paired with scaled down microfluidic chips, enabling production of single-cell capsules with characteristic size of approximately 20 μm.

Figure 4B:
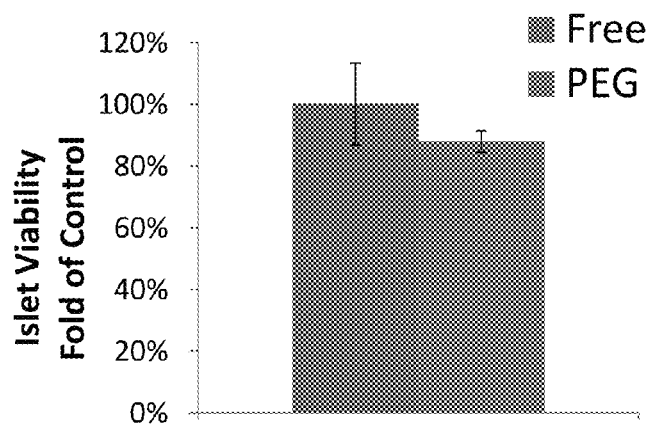
FIG. 4B is a bar graph showing islet viability (fold of control) for unmodified cells (left hand bar) and cells encapsulated in microgels (right hand bar).

Islets encapsulated with both microfluidic devices exhibited high cell viability (FIG. 4B) and detectable insulin secretion. Smaller capsules generated with the 400 μm device exhibited preferred diffusion kinetics for insulin secretion from islets encapsulated within the PEG hydrogel. Glucose-stimulated insulin secretion from PEG encapsulated islets is illustrated in FIG. 1E, where encapsulated islets perform comparably to unmodified islets. Minimal islet mass transplants allow for evaluation of technique efficacy with the minimal islet loading required to reverse diabetes.

Figure 4C:
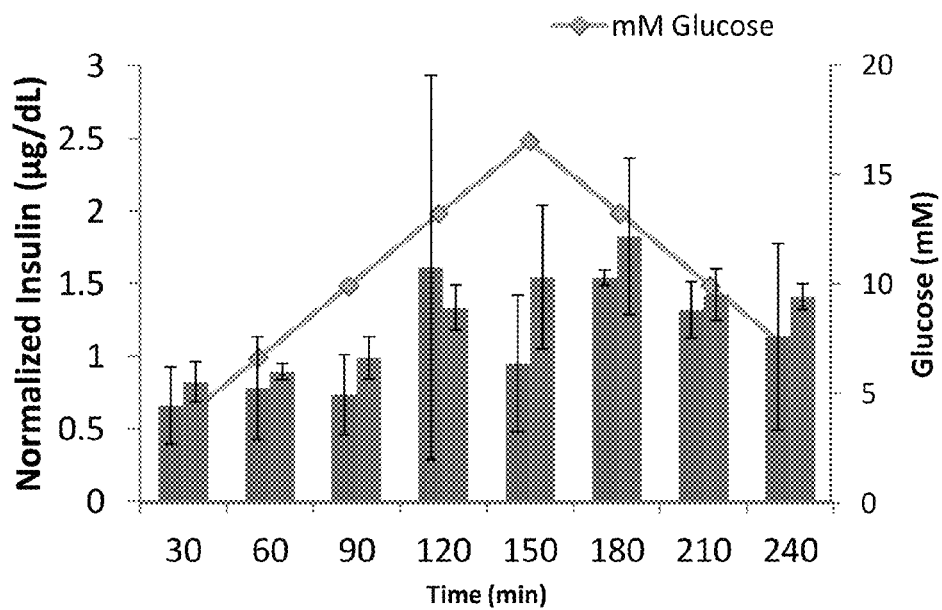
FIG. 4C is a bar graph showing glucose-stimulated insulin response (GSIR) (μg/dL) of islets encapsulated in PEG hydrogels as compared to unmodified islets at various time points. Glucose concentration (mM) administered over time is indicated by a line. For each time point, unmodified islets are represented with the left hand bar and islets encapsulated in PEG hydrogels are represented with the right hand bar.
Figure 4D:
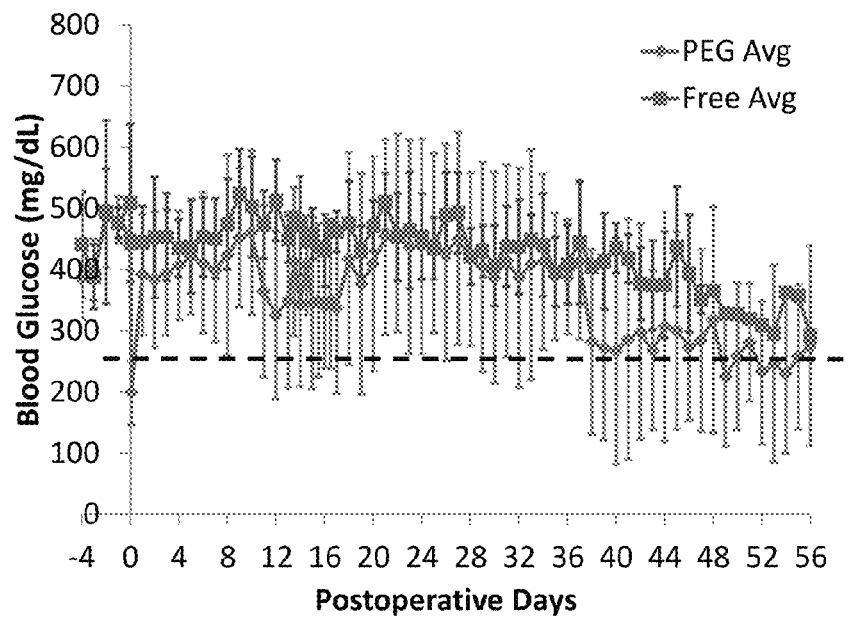
FIG. 4D is a line graph showing diabetes reversal time between unmodified (-■-) and PEG-encapsulated (-♦-) islets following syngeneic minimal islet mass transplant into diabetic mice.

Encapsulated cells achieved diabetes reversal in diabetic mice with 500-600 syngeneic islet equivalents (IEQ) (FIG. 4C).

Example 6

Controlled Release of Cargo Encapsulated in Microfluidic-Generated Biodegradable Microgel Droplets Materials and Methods Preparation of Microfluidic Device Silicon masters fabricated by the Stanford Microfluidics Foundry were used to cast PDMS microfluidic devices with a flow focusing geometry and 200 μm nozzles. Devices were bounded to glass slides after an air plasma treatment.

PEG-4MAL Microgel Formation

Microfluidic devices with flow focusing geometry were used to form the polymer droplets in a water in oil emulsion. Two different solutions of macromer 5% PEG-4MAL 20 kDa and crosslinker (GPQ (W) or VPM or GPQ (A) peptides) were prepared in PBS at a PEG-4MAL:crosslinker molar ratio of 2:1. The pH of both solutions was fixed at 6.5 and 4.5 respectively, without modification of the molar ratio, to control the kinetics of the gelation after contact of both phases in the microfluidic device. Devices with long outlet channels were used to increase the residence time of the generated droplets inside the device, in order to ensure the microgel formation before the polymer droplets leave the device. The generated microgels were washed several times in PBS.

Microgels Size

Microgels generated by using different biodegradable crosslinkers were observed under an optical microscope and representative images of each microgel were recorded for posterior analysis. Microparticle diameter of at least 20 microgels was measured for each crosslinker using ImageJ analysis software.

Protein Encapsulation and Release

Alexa fluor 488 IgG was encapsulated in PEG-4MAL hydrogels via microfluidics by using different crosslinkers. To do so, IgG protein was dissolved in 5% PEG-4MAL solution at 100 ug/ml and was posteriorly mixed, at a ratio of 2:1, with the corresponding crosslinker solution in the microfluidic device before being encapsulated by macromer droplet formation. The pH of both solutions was fixed to control the kinetics of the crosslinking reaction. After microgel formation, microparticles were washed several times in PBS and resuspended in 3 ml of PBS.

To evaluate the protein release from the microgels, the initial fluorescence of a 100 μl aliquot of the microparticle suspension was measured in a multimode plate reader. Collagenase I at a final concentration of 100 ug/ml was added to the microparticles and the concentration of the released protein in the supernatant at different time points was quantified by measuring the fluorescence of 100 μl aliquots.

Results

Figure 5A:
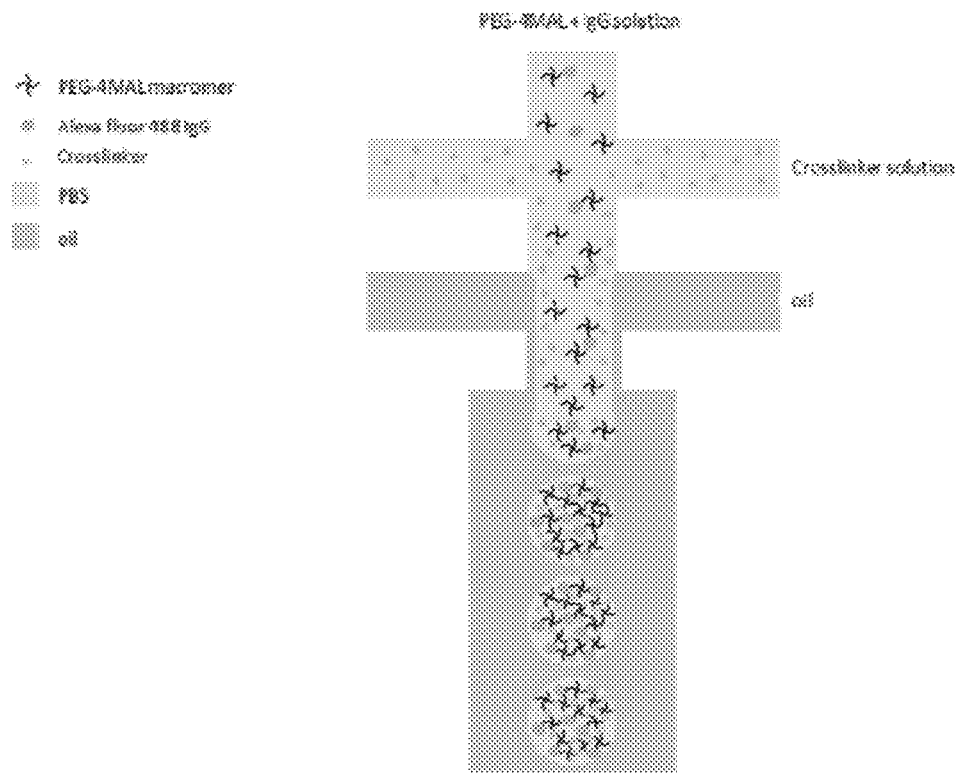
FIG. 5A a schematic of a microfluidic device with flow focusing geometry utilized to produce microgels according to the disclosed methods. A co-flowing oil phase shields an aqueous macromer solution, containing cargo, from the crosslinker-containing oil phase as the macromer solution approaches the flow focusing nozzle. After droplet formation, the crosslinker (e.g., DTT, or a cysteine-containing peptide) emulsion rapidly crosslinks macromere solution into cargo-laden microgels.

Macromer has a 4 arm PEG modified with a terminated maleimide group in each arm. Free thiol-containing molecules bind covalently to maleimide groups via Michael-type addition reaction (FIG. 1A). A flow focusing microfluidic device with 200 μm nozzle is used to produce microgels and encapsulate proteins. FIG. 5A is a schematic representation of the protein encapsulation via microfluidics on a flow focusing device. The solution of macromer PEG-4MAL and protein to be encapsulated is mixed with the crosslinker phase before the droplet formation. After droplet formation, in the outlet channel, peptide containing free cysteines reacts with the PEG-4MAL macromer to produce biodegradable crosslinked microgels.

Different biodegradable crosslinkers were used to produce PEG-4MAL microgels:

| Biodegradable crosslinkers | Peptide sequence | Mw |
|---|---|---|
| GPQ (W) (SEQ ID NO: 2) | GCRDGPQGIWGQDRCG (SEQ ID NO: 4) | 1704.88 |
| VPM | GCRDVPMSMRGGDRCG (SEQ ID NO: 5) | 1696.99 |
| GPQ (A) (SEQ ID NO: 3) | GCRDGPQGIAGQDRCG (SEQ ID NO: 6) | 1589.74 |

A microfluidic device with flow focusing geometry was used to obtain monodisperse biodegradable hydrogel microparticles:

| Crosslinker | Size |
|---|---|
| GPQ (W) (SEQ ID NO: 2) | 434.4 ± 69.6 |
| VPM | 386.2 ± 51.4 |
| GPQ (A) (SEQ ID NO: 3) | 401.6 ± 44.4 |

Figure 5B:
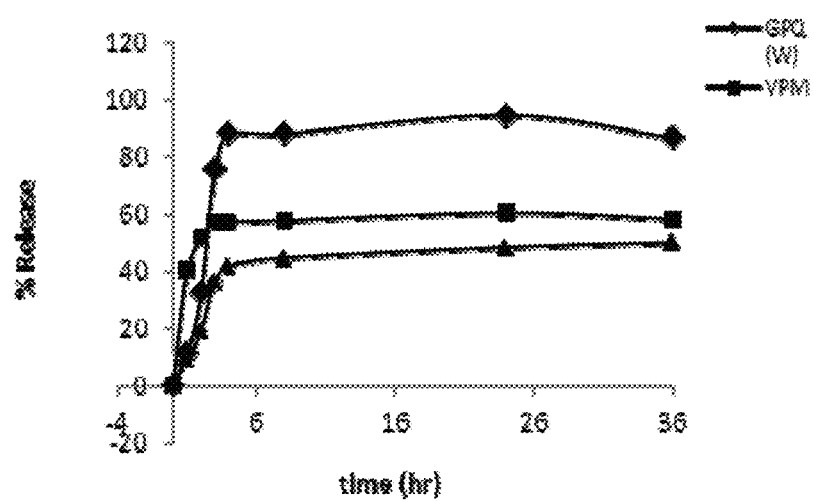
FIG. 5B is a line graph showing protein release from microgels crosslinked by different peptides crosslinkers (GPQ(W) (SEQ ID NO:2) (-♦-) and VPM (-■-) and GPQ(A) (SEQ ID NO:3) (-▲-)) over the time as they are degraded in the presence of protease (collagenase I).

Alexa fluor 488 IgG secondary antibody was encapsulated in the different microgels via microfluidics. The encapsulated protein was visualized using a confocal microscope and quantified by reading the fluorescence of a microparticle suspension in a plate reader. The protein release from the different microgels was evaluated over the time as they are degraded in the presence of protease (collagenase I) (FIG. 5B).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of encapsulating cargo in a microgel droplet comprising flowing a macromer phase, an oil phase, and a crosslinker phase through a flow focusing nozzle of a microfluidic device to form microgel droplets by oil and water emulsion, wherein the macromer phase comprises a macromer and a cargo in aqueous buffer; the oil phase comprises an oil-phase oil and an oil-phase surfactant; and the crosslinker phase comprises a crosslinker-phase oil, a crosslinker-phase surfactant, and a crosslinking agent, wherein the phases are pumped, injected, or passaged through the microfluidic device such that as the macromer phase approaches the flow focusing nozzle, the co-flowing oil phase shields the macromer from contact with the crosslinker phase until flow instability occurs and macromer phase droplets forms, wherein after flow instability occurs, the crosslinker diffuses from the crosslinker phase into the droplets in an effective amount to covalently crosslink the macromer into a microgel droplet encapsulating the cargo, and wherein the crosslinking is not ultraviolet (UV) initiated photopolymerization.

2. The method of claim 1, wherein the nozzle size and flow rates selected to produce droplets of a size between about 10 μm and 1,000 μm, inclusive.

3. The method of claim 2, wherein the flow rates of each of the phases is "X" nl/min, wherein "X" is an integer between about 100 and about 1,000,000.

4. The method of claim 2, wherein the nozzle size is between about 50 μm and 1,000 μm, inclusive.

5. The method of claim 1, wherein the macromer is a four arm maleimide-linked polyethylene glycol (PEG-4MAL).

6. The method of claim 5, wherein the crosslinker comprise a thiol that can be covalent crosslinked to the maleimide by a Michael-type additional reaction.

7. The method of claim 6, wherein the crosslinker is dithiothreitol (DTT) or a biodegradable peptide crosslinker compositing the amino acid sequence of SEQ ID NO:4, 5, or 6.

8. The method of claim 7, wherein the PEG-4MAL is "N" kDa wherein "N" is an integer between 1 and 50, inclusive.

9. The method of claim 8, wherein the microgel droplet is permeable to small molecules, but not to cells.

10. The method of claim 1, wherein the cargo encapsulated in each microgel droplet comprises one or more cells.

11. The method of claim 10, wherein the cargo encapsulated in each microgel droplet comprises a cluster of cells.

12. The method of claim 11, wherein the cluster of cells is an islet of pancreatic beta cells.

13. The method of claim 10, wherein the cells are stem cells.

14. The method of claim 1, wherein the cargo encapsulated in each microgel droplet comprises one or more bioactive agents.

15. The method of claim 14, wherein the one or more bioactive agents is selected from the group consisting of proteins, peptides, amino acids, nucleic acids, carbohydrates, lipids, small molecules, or combinations thereof.

16. The method claim 15, wherein the permeability of the microgel droplet allows slow or extended release of the bioactive agent.

17. The method of claim 8, wherein the macromer phase further comprises a bioactive agent comprising a thiol that is functionally linked to the macromer by a Michael-type addition reaction prior to crosslinking of the macromer into the microgel.

18. The method claim 17, wherein the bioactive agent can be released from the microgel by a protease in vivo.

* * * * *

SEQUENCE LISTING

```
<160> NUMBER OF SEQ ID NOS: 6

<210> SEQ ID NO 1
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 1

Gly Arg Gly Asp Ser Pro Cys
1               5

<210> SEQ ID NO 2
<211> LENGTH: 4
<212> TYPE: PRT
<213> ORGANISM: Artificial Sequence
<220> FEATURE:
<223> OTHER INFORMATION: synthetic polypeptide (abbreviation for SEQ ID
      NO:4)

<400> SEQUENCE: 2

Gly Pro Gln Trp
1

<210> SEQ ID NO 3
<211> LENGTH: 4
<212> TYPE: PRT
<213> ORGANISM: Artificial Sequence
<220> FEATURE:
<223> OTHER INFORMATION: Synthetic polypeptide (abbreviation for SEQ ID
      NO:6)

<400> SEQUENCE: 3

Gly Pro Gln Ala
```

```
<210> SEQ ID NO 4
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 4

Gly Cys Arg Asp Gly Pro Gln Gly Ile Trp Gly Gln Asp Arg Cys Gly
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 5

Gly Cys Arg Asp Val Pro Met Ser Met Arg Gly Gly Asp Arg Cys Gly
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 6

Gly Cys Arg Asp Gly Pro Gln Gly Ile Ala Gly Gln Asp Arg Cys Gly
1               5                   10                  15
```